US011903954B2

(12) United States Patent
Laser et al.

(10) Patent No.: US 11,903,954 B2
(45) Date of Patent: *Feb. 20, 2024

(54) METHOD OF TREATING UROLITHIASIS

(71) Applicant: Applaud Medical, Inc., San Francisco, CA (US)

(72) Inventors: Daniel J. Laser, San Francisco, CA (US); Alice Luong, San Francisco, CA (US); Robert G. Miotke, Gold River, CA (US)

(73) Assignee: APPLAUD MEDICAL, INC., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/879,267

(22) Filed: Aug. 2, 2022

(65) Prior Publication Data

US 2022/0395517 A1    Dec. 15, 2022

Related U.S. Application Data

(63) Continuation of application No. 17/155,537, filed on Jan. 22, 2021, now Pat. No. 11,464,792, which is a
(Continued)

(51) Int. Cl.
*A61K 31/685* (2006.01)
*A61K 9/00* (2006.01)
(Continued)

(52) U.S. Cl.
CPC .......... *A61K 31/685* (2013.01); *A61K 9/0034* (2013.01); *A61K 9/167* (2013.01);
(Continued)

(58) Field of Classification Search
None
See application file for complete search history.

(56) References Cited

U.S. PATENT DOCUMENTS 5,463,092 A    10/1995 Hostetler et al.
5,860,972 A *  1/1999 Hoang ............... A61B 18/26
                                              606/127
(Continued)

FOREIGN PATENT DOCUMENTS

CN    110269937 A    9/2019
EP    2 468 760 A1    6/2012
(Continued)

OTHER PUBLICATIONS

Pishchalnikov et al ("High-speed video microscopy and numerical modeling of bubble dynamics near a surface of urinary stone", The Journal of the Acoustical Society of America, vol. 146, p. 516-531 (2019)) (Year: 2019).*
(Continued)

*Primary Examiner* — Sin J Lee
(74) *Attorney, Agent, or Firm* — FENWICK & WEST LLP; Hayan Yoon; Brennan A. Murphy

(57) ABSTRACT

The present disclosure provides phospholipid-containing compounds, pharmaceutical compositions and microspheres that exhibit high affinity for mineralized metals. The present disclosure also provides strategies for using said compounds, compositions and microspheres in the treatment of nephrolithiasis or kidney stone disease, and methods of manufacturing and preparing said compounds and compositions.

16 Claims, 14 Drawing Sheets

Related U.S. Application Data continuation of application No. 16/775,253, filed on Jan. 28, 2020, now Pat. No. 10,953,023.

(51) Int. Cl.

| | |
|---|---|
| *A61K 9/16* | (2006.01) |
| *A61K 9/50* | (2006.01) |
| *A61K 41/00* | (2020.01) |
| *A61K 47/06* | (2006.01) |
| *A61K 47/26* | (2006.01) |
| *A61K 47/32* | (2006.01) |
| *A61K 47/54* | (2017.01) |
| *A61K 47/60* | (2017.01) |
| *A61K 47/69* | (2017.01) |
| *A61K 31/663* | (2006.01) |
| *A61P 13/04* | (2006.01) |
| *C07F 9/38* | (2006.01) |
| *C07F 9/40* | (2006.01) |

(52) U.S. Cl.
CPC .......... *A61K 9/5015* (2013.01); *A61K 9/5089* (2013.01); *A61K 41/0028* (2013.01); *A61K 47/06* (2013.01); *A61K 47/26* (2013.01); *A61K 47/32* (2013.01); *A61K 47/544* (2017.08); *A61K 47/60* (2017.08); *A61K 47/6925* (2017.08); *A61P 13/04* (2018.01); *C07F 9/3873* (2013.01); *C07F 9/405* (2013.01); *A61K 31/663* (2013.01)

(56) References Cited

U.S. PATENT DOCUMENTS

| | | | |
|---|---|---|---|
| 6,245,318 | B1 | 6/2001 | Klibanov et al. |
| 6,261,537 | B1 | 7/2001 | Klaveness et al. |
| 10,149,906 | B2 * | 12/2018 | Grubbs ................ A61K 9/1075 |
| 10,953,023 | B1 * | 3/2021 | Laser ................... A61K 9/0034 |
| 2007/0110674 | A1 | 5/2007 | Xu et al. |
| 2007/0207194 | A1 | 9/2007 | Grayburn et al. |
| 2007/0258908 | A1 | 11/2007 | Lanza et al. |
| 2008/0009561 | A1 | 1/2008 | Unger et al. |
| 2008/0045865 | A1 | 2/2008 | Kislev |
| 2008/0269668 | A1 | 10/2008 | Keenan et al. |
| 2008/0319375 | A1 | 12/2008 | Hardy |
| 2009/0136594 | A1 | 5/2009 | McLeroy et al. |
| 2009/0215729 | A1 | 8/2009 | Johnson et al. |
| 2010/0285112 | A1 | 11/2010 | Novobrantseva et al. |
| 2012/0201900 | A1 | 8/2012 | Borden et al. |
| 2013/0123781 | A1 | 5/2013 | Grubbs et al. |
| 2014/0010848 | A1 | 1/2014 | Kheir et al. |
| 2019/0200659 | A1 | 7/2019 | Smutzer et al. |
| 2019/0282695 | A1 | 9/2019 | Grubbs et al. |

FOREIGN PATENT DOCUMENTS

| | | |
|---|---|---|
| JP | 2009-280500 A | 12/2009 |
| WO | WO 1997/029782 A1 | 8/1997 |
| WO | WO 2001/09146 A1 | 2/2001 |
| WO | WO 2008/131217 A1 | 10/2008 |
| WO | WO 2009/055014 A2 | 4/2009 |
| WO | WO 2009/141823 A2 | 11/2009 |
| WO | WO 2012/094541 A2 | 7/2012 |
| WO | WO 2012/143739 A1 | 10/2012 |
| WO | WO 2016/205820 A1 | 12/2016 |
| WO | WO 2017/197726 A1 | 11/2017 |

OTHER PUBLICATIONS

Bhadane, S., "High Intensity Focused Ultrasound and Microbubble Induced Tissue Ablation: Effect of Treatment Parameters on Thermal Lesion Volume and Temperature," Thesis, Ryerson University, 2009, 104 pages.

Bhushan, K. R., et al., "Synthesis of Conjugatable Bisphosphonates for Molecular Imaging of Large Animals," Angewandte Chemie International Edition, 2007, pp. 7679-7971, vol. 46.

Chen et al., "Bone Targeted Delivery of SDF-1 via Alendronate Functionalized Nanoparticles in Guiding Stem Cell Migration," ACS Applied Materials & Interfaces (2018), vol. 10, Issue 28, p. 23700-23710.

Deelman, L. E., et al., "Targeted renal therapies through microbubbles and ultrasound," *Advanced Drug Delivery Reviews*, 2010, pp. 1369-1377, vol. 62.

Geers, B., et al., "Adeno-associated virus loaded microbubbles as a tool for targeted gene Delivery," *Journal of Controlled Release*, 2010, 148, e57-e73, p. e59 (abstract).

Hernot, S., et al., "Microbubbles in Ultrasound-triggered drug and gene delivery," *Advanced Drug Delivery Reviews*, 2008, pp. 1153-1166, vol. 60.

Hu, Y., et al., "Mesenchymal stem cells: A promising targeted-delivery vehicle in cancer gene Therapy," *Journal of Controlled Release*, 2010, pp. 154-162, vol. 147.

International Search Report and Written Opinion, Patent Cooperation Treaty Application No. PCT/US2012/052187, dated Jan. 28, 2013, 11 Pages.

International Search Report and Written Opinion, Patent Cooperation Treaty Application No. PCT/US2016/038428, dated Oct. 27, 2016, 16 Pages.

International Search Report and Written Opinion, Patent Cooperation Treaty Application No. PCT/US2020/015493, dated Apr. 14, 2020, 13 pages.

Khelfallah, S. K., et al., "Synthesis of novel polymerizable molecules bearing bisphonate," *Organic & Biomolecular Chemistry*, 2015, pp. 11382-11392, vol. 13.

Liu, Y., et al., "Encapsulated ultrasound microbubbles: Therapeutic application in drug/gene Delivery," *Journal of Controlled Release*, 2006, pp. 89-99, vol. 114.

Matheson Tri-Gas, Inc., "Material Safety Data Sheet, Substance: Perfluoropropane," 1989, [online] [Retrieved on Sep. 22, 2016] Retrieved from the Internet <URL: https://www.mathesongas.com/pdfs/msds/MAT18290.pdf>.

Mayer, C. R., et al., "Ultrasonic gene and drug delivery to the cardiovascular system," *Advanced Drug Delivery Reviews*, 2008, pp. 1177-1192, vol. 60.

McDonald, C. J., et al., "Hollow latex particles: synthesis and applications," *Advanced in Colloid and Interface Science*, 2002, pp. 181-213, vol. 99.

Mellema, M. et al., "PD22-11 Absence of Ureteral/Renal Injury Following Low Intensity Extracorporeal Acoustic Energy Lithotripsy With Stone-Targeting Microbubbles in an In Vivo Swine Model," *The Journal of Urology*, vol. 199, Issue 4S, Supplement, May 19, 2018, p. e479.

Pishchalnikov, Y. et al., "Experimental observations and numerical modeling of lipid-shell microbubbles with calcium-adhering moieties for minimally-invasive treatment of urinary stones," *Proceedings of Meetings on Acoustics*, vol. 35, 020008, Nov. 2018, pp. 1-11.

Ramaswamy, K. et al., "Targeted Microbubbles: A Novel Application for the Treatment of Kidney Stones," BJU International, 2015, John Wiley & Sons Ltd., pp. 9-16, vol. 116.

Rapoport, N. et al., "Multifunctional Nanoparticles for Combining Ultrasonic Tumor Imaging and Targeted Chemotherapy," Journal Natl. Cancer. Inst., Jul. 18, 2007, vol. 99, Issue 14, pp. 1095-1106.

Shi, Y., et al., "Multistep Targeted Nano Drug Delivery System Aiming at Leukemic Stem Cells and Minimal Residual Disease," Mol. Pharmaceutics, 2013, pp. 2479-2489, vol. 10.

Sirsi, S. et al., "Microbubble Compositions, Properties and Biomedical Applications," Bubble Sci. Eng. Technol., Nov. 2009, pp. 3-17, vol. 1, No. 1-2.

Tinkov, S., et al., "New doxorubicin-loaded phospholipid microbubbles for targeted tumor therapy: Part I—Formulation development and in-vitro characterization," Journal of Controlled Release, 2010, pp. 143-150, vol. 143.

Unger, E. C. et al., "Therapeutic applications of microbubbles," European Journal of Radiology, vol. 42, Iss. 2, May 2002, pp. 160-168.

(56) References Cited

OTHER PUBLICATIONS

Unger, E. C., et al., "Therapeutic applications of lipid-coated microbubbles," Advanced Drug Delivery Reviews, 2004, pp. 1291-1314, vol. 56.
Vachal, P. et al., "Synthesis and Study of Alendronate Derivatives as Potential Prodrugs of Alendronate Sodium for the Treatment of Low Bone Density and Osteoporosis," *Journal of Medicinal Chemistry*, vol. 49, Iss. 11, 2006, pp. 3060-3063.
Wu, T.Y. et al., "Advances in Ultrasound Technology for Environmental Remediation," SpringerBriefs in Green Chemistry for Sustainability, 2013, pp. 5-12.
Yoshizawa, S. et al., "High Intensity Focused Ultrasound Lithotripsy with Cavitating Microbubbles," Med. Biol. Eng. Comput., 2009, pp. 851-860, vol. 47.
United States Office Action, U.S. Appl. No. 17/879,285, dated Apr. 13, 2023, 15 pages.
European Patent Office, Extended European Search Report, European Patent Office Application No. 20917150.3, dated Oct. 18, 2023, 5 pages.

\* cited by examiner

METHOD OF TREATING UROLITHIASIS

CROSS-REFERENCE TO RELATED APPLICATIONS

This application is a continuation of U.S. application Ser. No. 17/155,537, filed Jan. 22, 2021, now issued as U.S. Pat. No. 11,464,792, which is a continuation of U.S. application Ser. No. 16/775,253, filed Jan. 28, 2020now issued as U.S. Pat. No. 10,953,023, which is hereby incorporated by reference in its entirety.

BACKGROUND OF THE INVENTION

Microspheres with fluid cores enclosed by thin shells made up of lipid, proteins, and/or sugars have been used in medical and therapeutic products. These micron-scale, gas-core particles, sometimes referred to as microparticles, have been administered systemically to increase the information content of echocardiogram. Microspheres can be particularly useful for opacifying the heart's left ventricle, allowing the echocardiogram to more precisely reveal details of aortic valve operation. The category of microsphere products designed to be used in this manner for disease diagnosis are often referred to as ultrasound contrast agents (UCAs). UCA usage, while making use of mechanical energy sources (e.g. the ultrasound producing the echocardiogram) and in which an associated microsphere mechanical response invariably occurs, typically do not rely, for their function, on tissue effects from the microsphere mechanical response, and in fact are often engineered to minimize tissue effects.

Microspheres can also be used in therapies in which the microsphere mechanical response, with either direct or indirect associated tissue effects, is central. For example, it has been suggested that for certain cancers, microspheres can be used for targeted delivery of chemotherapeutic agents. For the targeted delivery, microsphere design generally entails a combination of tumor-specific ligands in the shell structure and fluid-phase chemotherapeutic agents in the core. After administration, the tumor-specific ligands in the shells are expected to make microspheres accumulate in and around the tumor. A mechanical energy source can then be used to break open the microspheres, releasing the chemotherapeutic agents from the core.

Microsphere mechanical effects can also be used in therapies for pathological biomineralizations, as described in U.S. Publication No. 2013/0123781, which is incorporated by reference in its entirety herein. In these therapies, the microspheres are designed to produce pressure effects resembling those of shock wave lithotripsy, in which powerful shock waves are focused onto a stone in the kidney or ureter. In shockwave lithotripsy, the focused high-intensity pressure waves, with peak pressures above 100 megapascals, bring about cavitation effects that progressively erode, pit and fragment the stone. In microsphere-based lithotripsy, microspheres accumulating on the stone surface can exhibit cavitation effects with similar or greater pressures than those in conventional shockwave lithotripsy, but with input mechanical energies some two orders of magnitude lower (Pishchalnikov et al., 2018); less intense input acoustic energies, compared to conventional shockwave lithotripsy, can have a variety of advantages both from a clinical workflow and patient outcome standpoint. Microsphere accumulation on stone surfaces can be facilitated by the incorporation of bisphosphonate-like components into the microsphere shell.

The mechanical effects of microspheres can be used in treatment of a variety of medical conditions involving an abnormal or obstructive mass, such as kidney stones, urinary stones, biliary stones, blood clots, fibroids, cancerous tumors, and atheromatous plaques. The treatment methods allow minimally invasive treatments of the medical conditions by destroying or reducing this mass without injury to healthy tissues and minimizing the pain, discomfort, and risks associated with surgical or other invasive treatments.

Given the wide range of therapeutic application of microspheres, efforts have been made to develop improved components for therapeutic microspheres. Despite the efforts, there remains a need in the art for improved phospholipid compounds that are safe and therapeutically effective. Additionally, it is important to develop phospholipid compounds that can be produced in large quantities and high qualities for therapeutic and commercial use of therapeutic microspheres.

SUMMARY

The present disclosure provides compounds, pharmaceutical compositions, and microsphere particles (or microspheres or particles) that exhibit hydrophobicity and a high affinity for calcium and other metals in mineralized forms, including biomineralizations. Furthermore, the present disclosure provides methods of manufacturing and preparing the compounds, compositions and microsphere particles and methods of using them for treatment of medical conditions involving an abnormal or obstructive mass, e.g., nephrolithiasis or kidney stone disease. The methods described herein allows production of microspheres of high qualities in large scales, allowing therapeutic and commercial use of the therapeutic microspheres.

Accordingly, in a first aspect, the present disclosure provides a compound of Formula IV

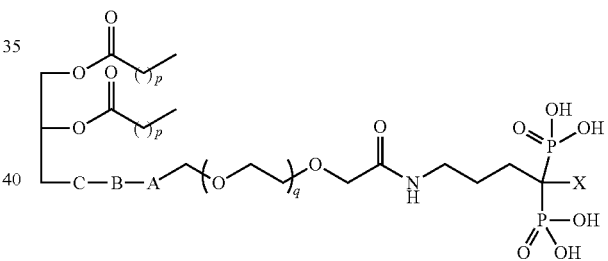

Formula IV or a salt, isomer, or salt of an isomer thereof, wherein:

p is from 10 to 30;

q is from 1 to 100;

C is selected from the group consisting of:

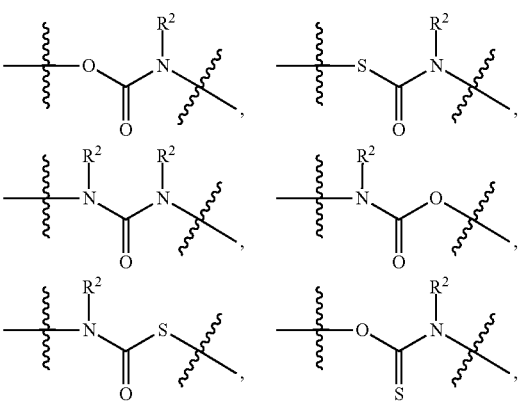

-continued

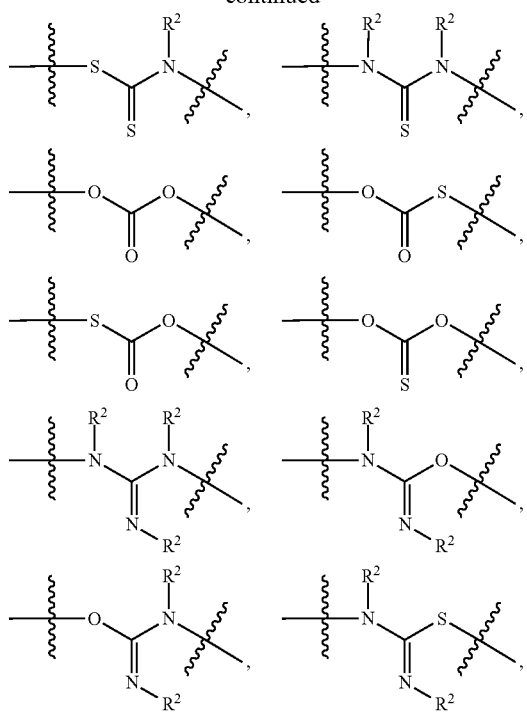

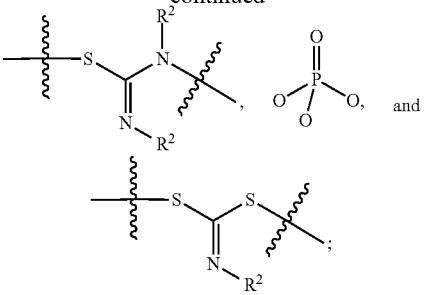

B is selected from the group consisting of: a covalent bond and an ethyl group;

A is selected from the group consisting of: a covalent bond, acyl, acylamino, aminoacyl, acyloxy, thioacyl, aminocarbonyl, aminoacyl carbonyloxy, aminothiocarbonyl, aminocarbonylamino, aminothiocarbonylamino, aminocarbonyloxy, aminosulfonyloxy, aminosulfonylamino, aminosulfonyl, amidino, and carboxy ester; and X is selected from the group consisting of: hydrogen, silyl, acyl, aminoacyl, thioacyl, aminocarbonyl, aminoacyl carbonyloxy, aminothiocarbonyl, aminosulfonyl, amidino, substituted sulfonyl, substituted sulfinyl, carboxy ester, phthalimido, $SO_3H$ and $PO_3H$.

In some embodiments, p is 14 or 16, and q is from 38 to 50.

In some embodiments, the compound of Formula IV is the compound of Formula I

Formula I

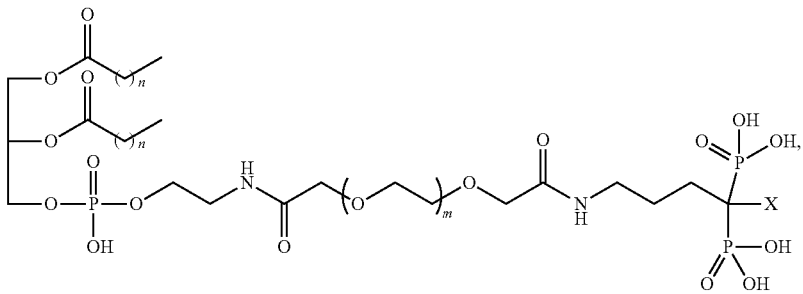

or a salt, isomer, or salt of an isomer thereof, wherein:
n is from 10 to 30, and
m is from 1 to 100.

In some embodiments, n is 14 or 16 and m is from 38 to 50.

In some embodiments, the compound of Formula I is the compound of Formula Ia

Formula Ia

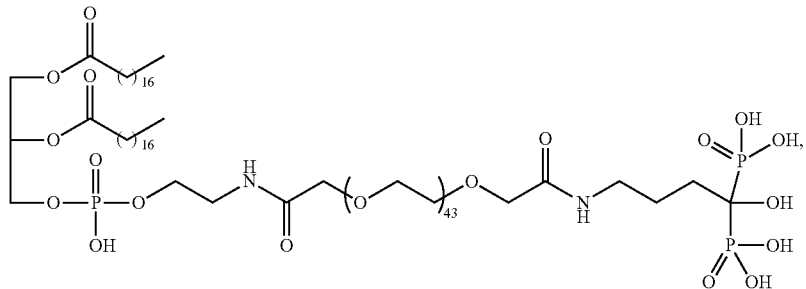

or a salt, isomer, or salt of an isomer thereof thereof.

In some embodiments, the compound of Formula I is the compound of Formula Ib

Formula Ib

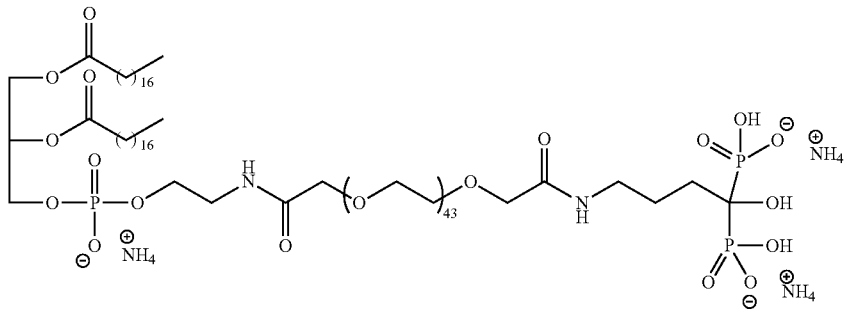

In the second aspect, the present disclosure provides a pharmaceutical composition, comprising:

a compound of Formula IV

Formula IV

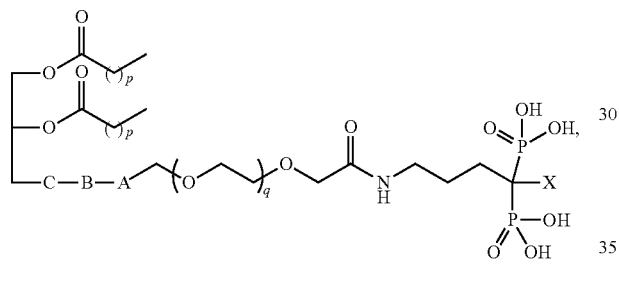

or a pharmaceutically acceptable salt, isomer, or salt of an isomer thereof;

wherein:

p is from 10 to 30, q is from 1 to 100,

C is selected from the group consisting of:

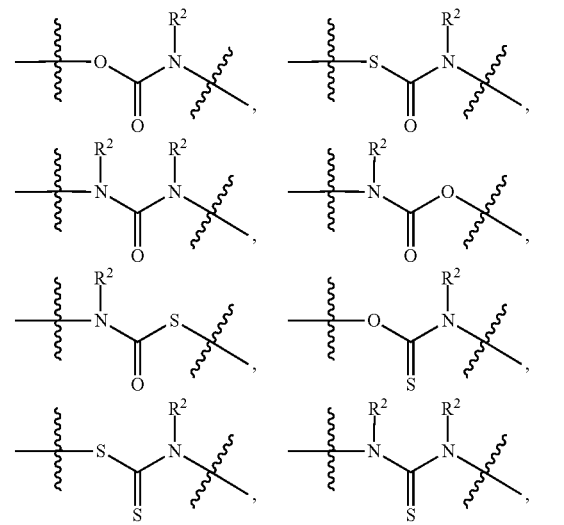

-continued

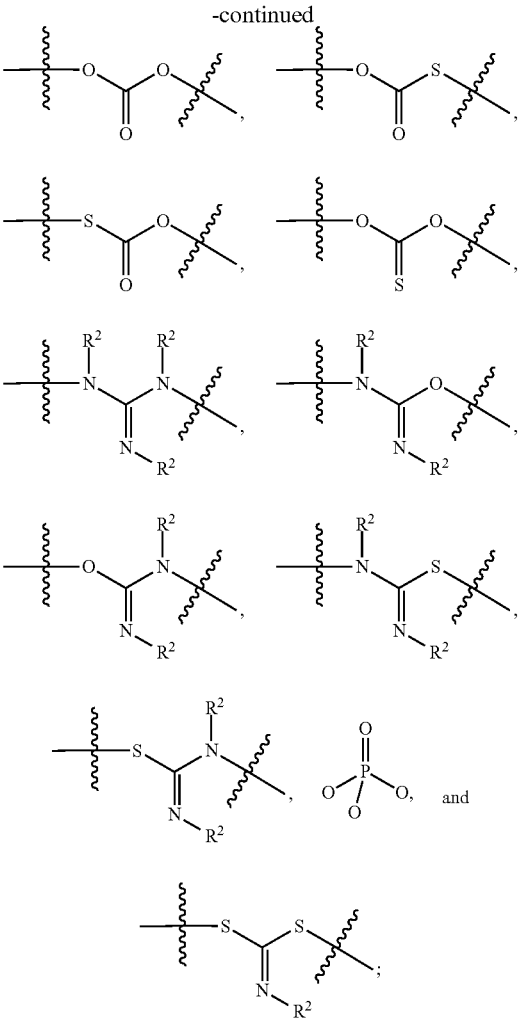

B is selected from the group consisting of: a covalent bond and an ethyl group;

A is selected from the group consisting of: a covalent bond, acyl, acylamino, aminoacyl, acyloxy, thioacyl, aminocarbonyl, aminoacyl carbonyloxy, aminothiocarbonyl, aminocarbonylamino, aminothiocarbonylamino, aminocarbonyloxy, aminosulfonyloxy, aminosulfonylamino, aminosulfonyl, amidino, amide, and carboxy ester; and X is selected from the group consisting of: hydrogen, silyl, acyl, aminoacyl, thioacyl, aminocarbonyl, aminoacyl carbonyloxy, aminothiocarbonyl, aminosulfonyl, amidino, substituted sulfonyl, substituted sulfinyl, carboxy ester, phthalimido, OH SO$_3$H and PO$_3$H.

In some embodiments, p is 14 or 16, and q is from 38 to 50.

In some embodiments, the composition further comprises: a compound of Formula II

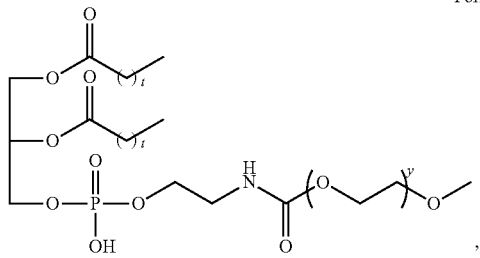

Formula II or a pharmaceutically acceptable salt, isomer, or salt of an isomer thereof;

a compound of Formula III

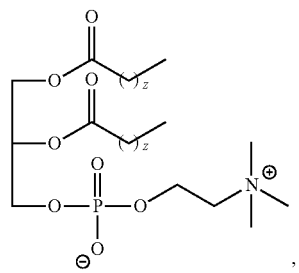

Formula III or a pharmaceutically acceptable salt, isomer, or salt of an isomer thereof;
wherein:
t is from 10 to 30,
y is from 1 to 100, and
z is from 10 to 30.

In some embodiments, t is 14 or 16, z is 14 or 16, and y is from 38 to 50.

In some embodiments, the compound of Formula IV is a compound of Formula I

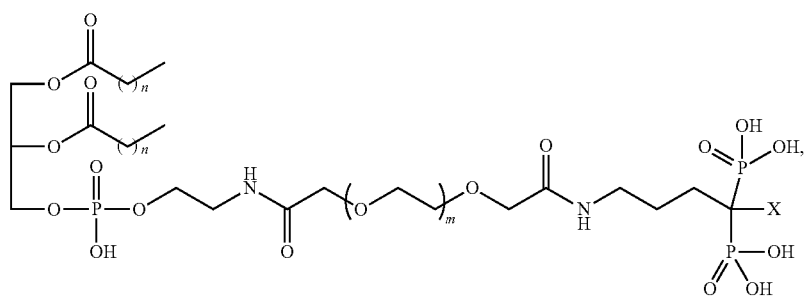

Formula I or a pharmaceutically acceptable salt, isomer, or salt of an isomer thereof, wherein:
n is from 10 to 30, and
m is from 1 to 100.

In some embodiments, n is 14 or 16, and m is from 38 to 50.

In some embodiments, the compound of Formula I is the compound of Formula Ia

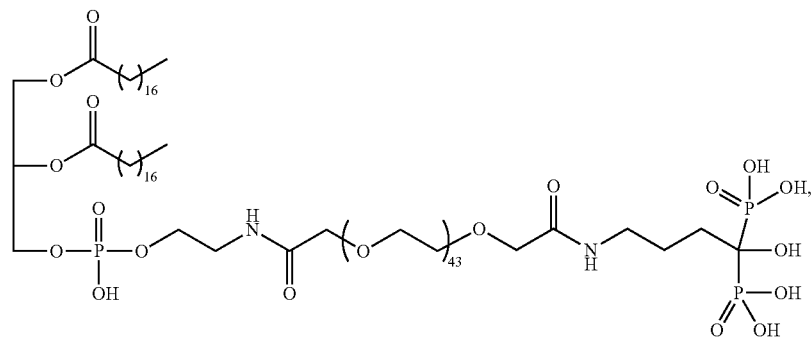

Formula Ia or a pharmaceutically acceptable salt, isomer, or salt of an isomer thereof.

In some embodiments, the compound of Formula Ia is the compound of Formula Ib

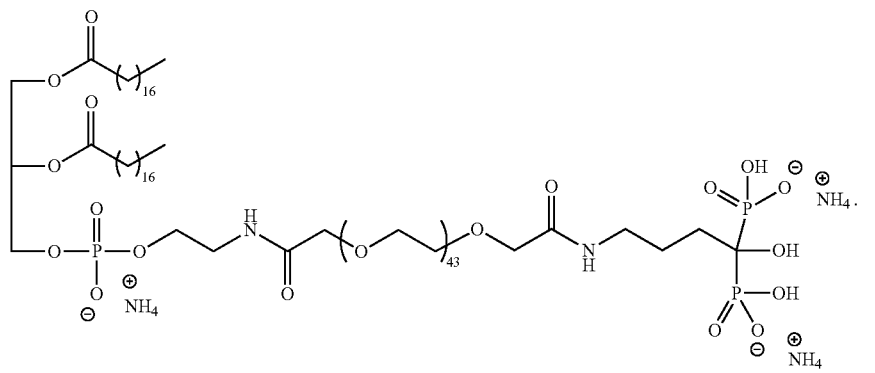

Formula Ib

In some embodiments, the composition further comprises a fluid with a normal boiling point less than 30° C. and, optionally, at least one pharmaceutically acceptable excipient. In some embodiments, the fluid is a gas at body temperature. In some embodiments, the fluid has low solubility in aqueous solutions. In some embodiments, the fluid is air, nitrogen, argon, carbon dioxide ($CO_2$), sulfur hexafluoride, a fluorinated $C_{1-6}$ alkane, or a combination thereof. In some embodiments, the fluorinated $C_{1-6}$ alkane is selected from octafluoropropane, n-decafluorobutane, and dodecafluoropentane.

In some embodiments, the composition comprises 0.01-5 mol % of the compound of Formula IV or Formula I, or a salt, isomer, or salt of an isomer thereof. In some embodiments, the composition comprises 5-9.9 mol % of the compound of Formula II, or a salt, isomer, or salt of an isomer thereof. In some embodiments, the composition comprises 80-95 mol % of the compound of Formula III, or a salt, isomer, or salt of an isomer thereof. In some embodiments, the composition comprises no more than 5 mol % of the compound of Formula IV or Formula I, or a salt, isomer, or salt of an isomer thereof. In some embodiments, the composition comprises no more than 10 mol % of the compound of Formula II, or a salt, isomer, or salt of an isomer thereof. In some embodiments, In some embodiments, the composition comprises no more than 95 mol % of the compound of Formula III, or a salt, isomer, or salt of an isomer thereof.

In some embodiments, the composition comprises the ammonium salt of the compound of Formula IV or Formula I. In some embodiments, the composition comprises the ammonium salt of the compound of Formula II.

In some embodiments, the molecular weight of the compound of Formula IV or Formula I is 1,500 to 5,000 Daltons. In some embodiments, the molecular weight of the compound of Formula II is 1,500 to 5,000 Daltons. In some embodiments, the molecular weight of the compound of Formula III is 500 to 2,000 Daltons.

In some embodiments, the molar ratio of the compound of Formula IV or Formula I to the compound of Formula II ranges from 1:100 to 1:1. In some embodiments, the molar ratio of the compound of Formula II to the compound of Formula III ranges from 1:20 to 1:8.

In some embodiments, the compound of Formula Ia is a compound of Formula Ib

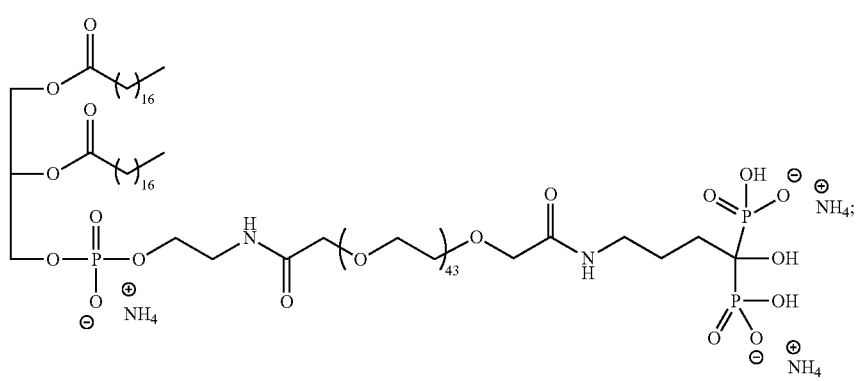

Formula Ib the compound of Formula II is a compound of Formula IIb

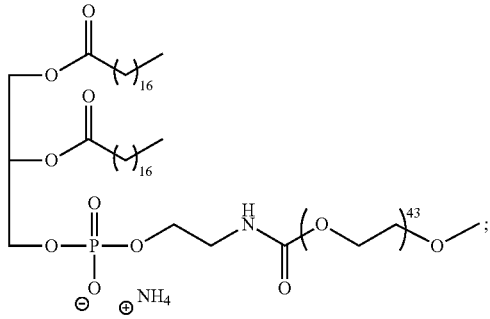

Formula IIb the compound of Formula III is the compound of Formula IIIa

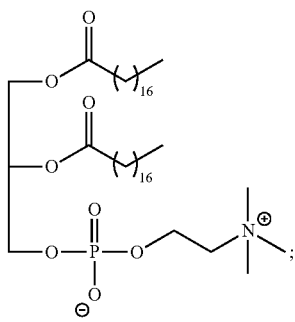

Formula IIIa and the composition comprises the fluid, wherein the fluid is n-decafluorobutane.

In some embodiments, the average molecular weight of the compound of Formula Ib is about 3200 Daltons. In some embodiments, the average molecular weight of the compound of Formula IIb is about 2800 Daltons. In some embodiments, the average molecular weight of the compound of Formula IIIa is about 790 Daltons.

In some embodiments, the composition comprises 0.01-5 mol % of a compound of Formula Ib. In some embodiments, the composition comprises 5-9.9 mol % of a compound of Formula IIb. In some embodiments, the composition comprises 80-95 mol % of the compound of Formula IIIa. In some embodiments, the composition comprises no more than 5 mol % of a compound of Formula Ib. In some embodiments, the composition comprises no more than 10 mol % of a compound of Formula IIb. In some embodiments, the composition comprises no more than 95 mol % of the compound of Formula IIIa.

In some embodiments, the molar ratio of the compound of Formula Ib to the compound of Formula IIb ranges from 1:100 to 1:1. In some embodiments, the molar ratio of the compound of Formula IIb to the compound of Formula IIIa ranges from 1:20 to 1:8.

In some embodiments, the composition is capable of forming microspheres in the presence of water. In some embodiments, the composition comprises microspheres. In some embodiments, the microspheres comprise the compound of Formula Ib, the compound of Formula IIb, and the compound of Formula IIIa.

In some embodiments, the microspheres have a mean diameter of about 0.5 micron to about 10 microns. In some embodiments, the microspheres have a mean diameter of about 1 micron to about 5 microns.

In some embodiments, the composition comprises trehalose and PLASDONE K12 as excipients. In some embodiments, the composition comprises microspheres existing as lyophilized dry powder or as water-free concentrate.

In another aspect, the present disclosure provides a method of manufacturing microspheres, the method comprising:

(a) preparing a formulation for making microspheres comprising:

a compound of Formula I

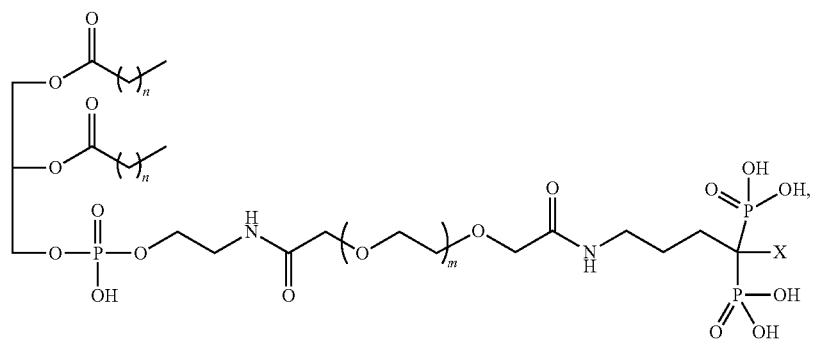

Formula I or a salt, isomer, or salt of an isomer thereof;

a compound of Formula II

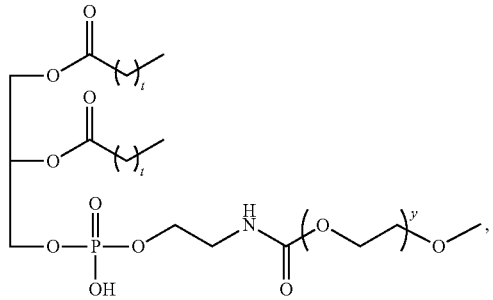

Formula II or a salt, isomer, or salt of an isomer thereof;
a compound of Formula III

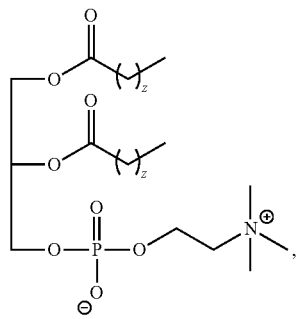

Formula III or a salt, isomer, or salt of an isomer thereof;
optionally, at least one pharmaceutically acceptable excipient; and
water,
wherein:
n is from 10 to 30,
m is from 1 to 100,
t is from 10 to 30,
y is from 1 to 100,
z is from 10 to 30, and
X is selected from the group consisting of: hydrogen, silyl, acyl, aminoacyl, thioacyl, aminocarbonyl, aminoacyl carbonyloxy, aminothiocarbonyl, aminosulfonyl, amidino, substituted sulfonyl, substituted sulfinyl, carboxy ester, phthalimido, OH, $SO_3H$ and $PO_3H$.

In some embodiments, the method further comprises:
(b) combining the formulation of step (a) with a fluid with a normal boiling point of less than 30° C. in a vessel; and
(c) agitating the vessel containing the formulation and fluid from step (b) thereby obtaining microspheres.

In some embodiments, the method further comprises:
(d) processing the microsphere solution from step (c) to lengthen its shelf life or expand the range of environmental conditions for storage.

In some embodiments, the method further comprises:
(e) stoppering the vessel comprising the microspheres from step (c) or (d), optionally under vacuum.

In some embodiments, the formulation of step (a) is filtered prior to step (b). In some embodiments, the processing step (d) is lyophilizing the microsphere solution.

In some embodiments, the vessel is a unit dosage container. In some embodiments, the fluid is n-decafluorobutane. In some embodiments, the headspace of the capped vessel is filled with n-decafluorobutane.

In some embodiments, the mean diameter of the microspheres from step (c) is about 0.1 to 1000 μm. In some embodiments, the mean diameter of the microspheres from step (c) is about 0.1 to 100 μm. In some embodiments, the mean diameter of the microspheres from step (c) is about 0.1 to 30 μm. In some embodiments, the mean diameter of the microspheres from step (c) is about 0.7 to 10 μm.

In some embodiments, the processing step (d) is lyophilizing the microsphere solution and loss of microspheres during lyophilization is no more than 25%. In some embodiments, the loss of the microspheres during lyophilization is no more than 15% or no more than 10%.

In some embodiments, the molecular weight of the compound of Formula I is 1,500 to 5,000 Daltons. In some embodiments, the molecular weight of the compound of Formula II is 1,500 to 5,000 Daltons. In some embodiments, the molecular weight of the compound of Formula III is 500 to 2,000 Daltons.

In some embodiments, the molar ratio of the compound of Formula I to the compound of Formula II in the formulation ranges from 1:100 to 1:1. In some embodiments, the molar ratio of the compound of Formula II to the compound of Formula III in the formulation ranges from 1:20 to 1:8.

In some embodiments, the microspheres from step (c) comprise 0.01-5 mol % of a compound of Formula I. In some embodiments, the microspheres from step (c) comprise 5-9.9 mol % of a compound of Formula II. In some embodiments, the microspheres from step (c) comprise 80-95 mol % of the compound of Formula III. In some embodiments, the microspheres from step (c) comprise no more than 5 mol % of the compound of Formula I. In some embodiments, the microspheres from step (c) comprise no more than 10 mol % of the compound of Formula II. In some embodiments, the microspheres from step (c) comprise no more than 95 mol % of the compound of Formula III.

In some embodiments, the compound of Formula I is a compound of Formula Ib; the compound of Formula II is a compound of Formula IIb; and the compound of Formula III is the compound of Formula IIIa.

In some embodiments, the average molecular weight of the compound of Formula Ib is about 3200 Daltons. In some embodiments, the average molecular weight of the compound of Formula IIb is about 2800 Daltons. In some embodiments, the average molecular weight of the compound of Formula IIIa is about 790 Daltons.

In some embodiments, the microspheres from step (c) comprise 0.01-5 mol % of the compound of Formula Ib. In some embodiments, the microspheres from step (c) comprise 5-9.9 mol % of the compound of Formula IIb. In some embodiments, the microspheres from step (c) comprise 80-95 mol % of the compound of Formula IIa.

In some embodiments, the microspheres from step (c) comprise no more than 5 mol % of the compound of Formula Ib. In some embodiments, the microspheres from step (c) comprise no more than 10 mol % of the compound of Formula IIb. In some embodiments, the microspheres from step (c) comprise no more than 95 mol % of the compound of Formula IIIa.

In some embodiments, the molar ratio of the compound of Formula Ib to the compound of Formula IIb in the microspheres from step (c) ranges from 1:100 to 1:1. In some embodiments, the molar ratio of the compound of Formula IIb to the compound of Formula IIIa in the microspheres from step (c) ranges from 1:20 to 1:8.

In yet another aspect, the present disclosure provides a unit dosage container, comprising: a therapeutically effective amount of the pharmaceutical composition provided herein. In some embodiments, the compound of Formula I is a compound of Formula Ib. In some embodiments, the compound of Formula II is a compound of Formula IIb. In some embodiments, the compound of Formula III is the compound of Formula IIa. In some embodiments, the fluid is air, $CO_2$, sulfur hexafluoride, a fluorinated $C_{1-6}$ alkane, or a combination thereof. In some embodiments, the fluorinated $C_{1-6}$ alkane is selected from octafluoropropane, n-decafluorobutane, and dodecafluoropentane. In some embodiments, the fluid is n-decafluorobutane. In some embodiments, the composition comprises trehalose and PLASDONE K12 as excipients. In some embodiments, the composition further comprises a buffering solution wherein the buffering solution is a phosphate salt. In some embodiments, the buffering solution comprises saline without calcium and magnesium.

In some embodiments, the composition is capable of forming microspheres in the presence of water. In some embodiments, the composition comprises microspheres. In some embodiments, the microspheres exist as lyophilized dry powder or as water-free concentrate. In some embodiments, the container is prepared by the process provided herein. In some embodiments, the container is sealed by a crimp-top cap fitted with a septum. In some embodiments, the container is airtight.

In one embodiment, the present disclosure provides a kit comprising: at least one unit dosage container as described above, and instructions for using said kit.

In some embodiments, the unit dosage container comprises trehalose and PLASDONE K12 as excipients. In some embodiments, the kit further comprises a container comprising an aqueous solution. In some embodiments, the aqueous solution is sterile water. In some embodiments, the aqueous solution is a saline solution ready for perfusion. In some embodiments, the kit further comprises a syringe. In some embodiments, the kit further comprises a needle fitted for the syringe. In some embodiments, the kit comprises a needle-free syringe comprising a sharp tip. In some embodiments, the needle or the sharp tip is capable of piercing through a septum cap.

In some embodiments, the kit further comprises a container comprising a fluid having a normal boiling point of less than 30° C., optionally wherein the container is a syringe. In some embodiments, the fluid is air, nitrogen, argon, $CO_2$, sulfur hexafluoride, a fluorinated $C_{1-6}$ alkane, or a combination thereof. In some embodiments, the fluorinated $C_{1-6}$ alkane is selected from octafluoropropane, n-decafluorobutane, and dodecafluoropentane. In some embodiments, the fluid is n-decafluorobutane.

In some embodiments, the kit further comprises at least one gel pad and ultrasound gel. In some embodiments, the kit further comprises an apparatus selected from Mix2Vial® apparatus and a vented vial adapter.

Another aspect of the present disclosure provides a method of reconstituting microspheres, wherein the method comprises:
  (a) adding a sufficient amount of water or a saline solution to the microspheres inside the container of the present disclosure,
  (b) optionally, adding a volume of a fluid having a normal boiling point of less than 30° C. to the container of step (a); and
  (c) optionally shaking the container of step (a) or step (b).

In some embodiments, the method further comprises a step of filling the container with gas before step (a). In some embodiments, the amount of water or the saline solution is no more than 100 milliliters. In some embodiments, the amount of the water or the saline solution added is sufficient to produce a homogeneous mixture comprising the reconstituted microspheres. In some embodiments, the shaking of the container lasts no more than 180 seconds.

In yet another aspect, the present disclosure provides a method of treating urolithiasis, the method comprising: administering to a subject with urolithiasis an effective amount of the pharmaceutical composition, microspheres, or the reconstituted microsphere solution disclosed herein so as to bring the microspheres into contact with the urinary stone, and directionally applying an energy, at a frequency that excites the fluid within the microspheres, to the urinary stone within the subject.

In some embodiments, the reconstituted microsphere solution is administered into the ureter of the subject through a urinary catheter. In some embodiments, the energy is in the form of electromagnetic, acoustic, microwave, photonic, or other forms. In some embodiments, the energy is ultrasonic.

In some embodiments, the ultrasonic energy is in the frequency range from 100 kilohertz (kHz) to 2 megahertz (MHz). In some embodiments, the ultrasonic energy is associated with peak pressures in the range 0.1 MPa to 10 MPa. In some embodiments, the energy is applied for a sufficient amount of time to fragment the urinary stone.

In some embodiments, the amount of time is no more than 100 minutes. In some embodiments, the amount of time is no more than 90 minutes. In some embodiments, the amount of time is no more than 80 minutes. In some embodiments, the amount of time is no more than 70 minutes. In some embodiments, the amount of time is no more than 60 minutes. In some embodiments, the amount of time is no more than 50 minutes. In some embodiments, the amount of time is no more than 40 minutes. In some embodiments, the amount of time is no more than 30 minutes. In some embodiments, the amount of time is no more than 25 minutes. In some embodiments, the amount of time is no more than 20 minutes. In some embodiments, the amount of time is no more than 15 minutes. In some embodiments, the amount of time is no more than 10 minutes.

In some embodiments, the applied energy causes a change in volume of the reconstituted microspheres or other cavitation effects of the microspheres. In some embodiments, the cavitation of the microspheres causes pressure gradient changes and other mechanical effects in the urinary stone around the reconstituted microspheres. In some embodiments, the pressure gradient changes and other mechanical effects are capable of fragmenting urinary stones. In some embodiments, the subject is human.

In one aspect, the present disclosure provides a reconstituted microsphere solution for use in the treatment of urolithiasis, wherein an effective amount of the said microsphere solution is administered to a subject so as to bring the microparticles into contact with the urinary stone; and an energy is directionally applied, at a frequency that excites the fluid within the microsphere, to the urinary stone within the subject.

In some embodiments, the reconstituted microsphere solution is administered into the ureter of the subject through a urinary catheter. In some embodiments, the energy is in the form of electromagnetic, acoustic, microwave, photonic, laser, or other forms. In some embodiments, the energy is ultrasonic.

In some embodiments, the ultrasonic energy is in the frequency range from 100 kilohertz (kHz) to 2 megahertz (MHz). In some embodiments, the ultrasonic energy is associated with peak pressures in the range 0.1 MPa to 10 MPa.

In some embodiments, the energy is in the form of laser. In some embodiments, the laser energy has a wave length in the infrared range from 1000 nm to 2500 nm. In some embodiments, the laser energy is capable of vaporizing intraluminal liquid, thereby capable of producing an associated acoustic wave. In some embodiments, the laser energy has a frequency in the range between 1 kHz to 1 MHz.

In some embodiments, the energy is applied for a sufficient amount of time to fragment the urinary stone. In some embodiments, the amount of time is no more than 100 minutes. In some embodiments, the amount of time is no more than 90 minutes. In some embodiments, the amount of time is no more than 80 minutes. In some embodiments, the amount of time is no more than 70 minutes. In some embodiments, the amount of time is no more than 60 minutes. In some embodiments, the amount of time is no more than 50 minutes. In some embodiments, the amount of time is no more than 40 minutes. In some embodiments, the amount of time is no more than 30 minutes. In some embodiments, the amount of time is no more than 25 minutes. In some embodiments, the amount of time is no more than 20 minutes. In some embodiments, the amount of time is no more than 15 minutes. In some embodiments, the amount of time is no more than 10 minutes.

In some embodiments, the applied energy causes a change in volume of the reconstituted microspheres or other cavitation effects of the microspheres. In some embodiments, the cavitation of the microspheres causes pressure gradient changes and other mechanical effects in the urine around the reconstituted microspheres. In some embodiments, the pressure gradient changes and other mechanical effects are capable of fragmenting urinary stones. In some embodiments, the subject is human.

BRIEF DESCRIPTION OF THE SEVERAL VIEWS OF THE DRAWINGS

These and other features, aspects, and advantages of the present invention will become better understood with regard to the following description, and accompanying drawings, where.

DETAILED DESCRIPTION OF THE INVENTION

Definitions

Figure 1:
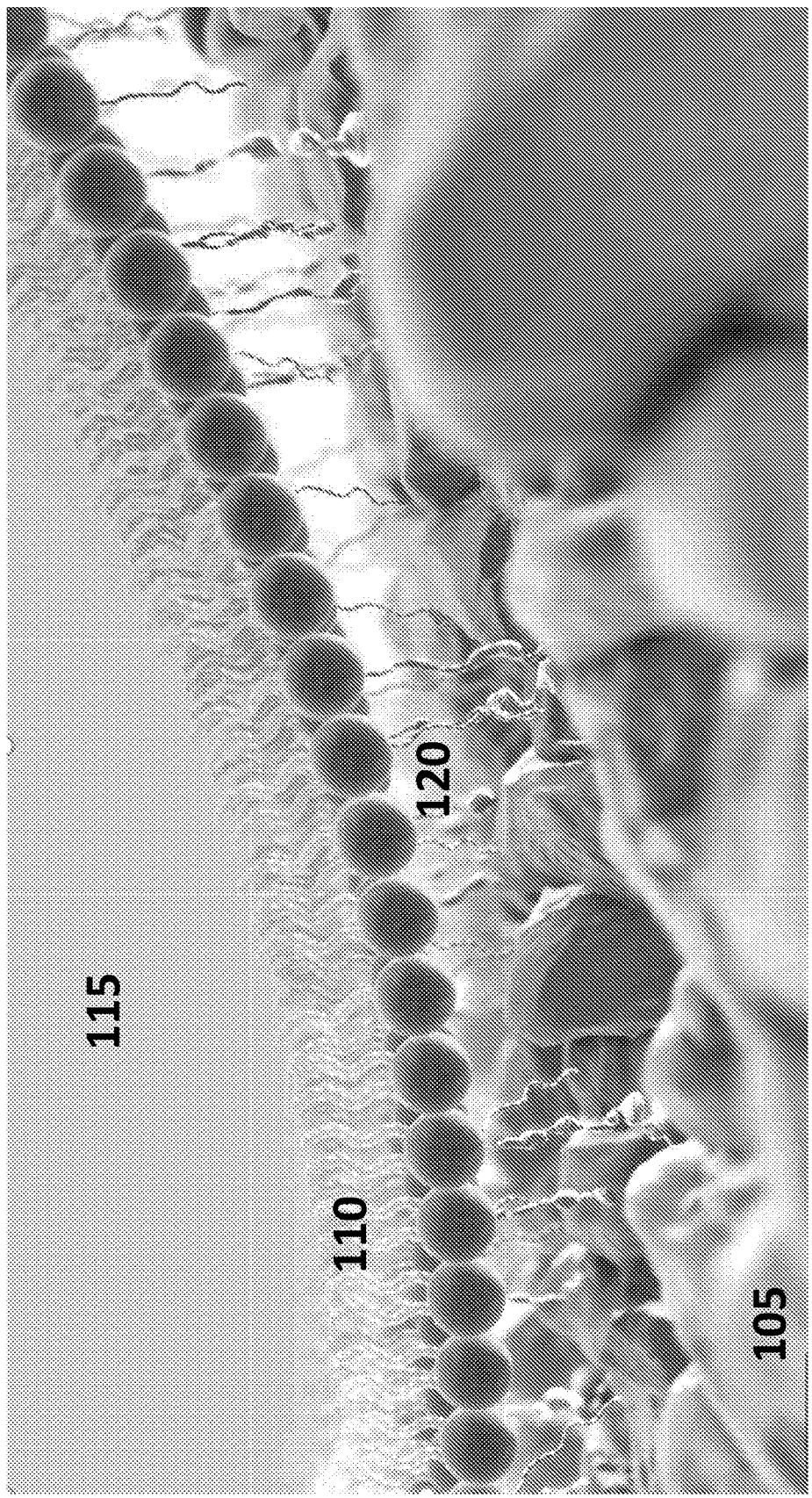
FIG. 1 shows a cutaway schematic of an exemplary microsphere attached to a mineralized material 105, including the accumulation-facilitating microsphere shell constituents 120, the microsphere lipid shell 110, and microsphere fluid core 115.

Unless otherwise defined herein, all technical and scientific terms used herein have the meaning commonly understood by a person skilled in the art to which this invention pertains.

The term "subject" refers to any mammal including humans, and mammals such as those animals of veterinary and research interest that are including, but not limited to: simians, cattle, horses, dogs, cats, and rodents.

The term "treating" or "treatment of" a disorder or disease refers to taking steps to alleviate the symptoms of the disorder or disease, e.g., reduction, destruction or removal of an abnormal or obstructive mass such as kidney stones, urinary stones, biliary stones, blood clots, fibroids, cancerous tumors, and atheromatous plaques, or otherwise obtain some beneficial or desired results for a subject, including clinical results. Any beneficial or desired clinical results may include, but are not limited to, alleviation or amelioration of one or more symptoms of the disorder or disease; diminishment of the extent of the disease; delay or slowing disease progression; amelioration, palliation, or stabilization of the disease state; or other beneficial results.

The term "effective amount" means an amount sufficient to produce a desired effect.

The term "sufficient amount" means an amount sufficient to produce a desired effect.

The term "therapeutically effective amount" is an amount that is effective to ameliorate or reduce a symptom of a disease.

The term "reduction" of a symptom or symptoms (and grammatical equivalents of this phrase) refers to decreasing the severity or frequency of the symptom(s), or elimination of the symptom(s).

The term "cavitational effect" as used herein refers to an effect sufficient to cause reduction or destruction of an abnormal or obstructive mass in vivo such as kidney stones, urinary stones, biliary stones, blood clots, fibroids, cancerous tumors, and atheromatous plaques.

The term "PL2kS" as used herein refers to the compound 1,2-distearoyl-sn-glycero-3-phosphoethanolamine-N-[methoxy(polyethylene glycol)-2000-alendronate] (ammonium salt), which is also disclosed as the compound of Formula Ib herein.

The term "DSPE-PEG2K" as used herein refers to the compound 1,2-distearoyl-sn-glycero-3-phosphoethanolamine-N-[methoxy(polyethylene glycol)-2000] (ammonium salt), which is also disclosed as the compound of Formula IIb herein.

The term "DSPC" as used herein refers to the compound 1,2-distearoyl-sn-glycero-3-phosphocholine, which is also disclosed as the compound of Formula IIIa herein.

The practice of the present invention includes the use of conventional techniques of organic chemistry, molecular biology (including recombinant techniques), microbiology, cell biology, biochemistry and immunology, which are within the skill of the art.

In this application, reference will be made to a number of technical designations. All numerical designations, e.g., pH, temperature, time, concentration, and weight, including ranges of each thereof, are approximations that typically may be varied (+) or (−) by increments of 0.1, 1.0, or 10.0, as appropriate. All numerical designations may be understood as preceded by the term "about." Reagents described herein are exemplary and equivalents of such may be known in the art.

Compounds utilized in the present invention may possess asymmetric carbon atoms (optical centers) or double bonds; the racemates, diastereomers, geometric isomers, regioisomers and individual isomers (e.g., separate enantiomers) are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example, and without limitation, tritium ($^3$H), iodine-125 ($^{125}$I), or carbon-14 ($^{14}$C). All isotopic variations of the compounds of the present invention, whether radioactive or not, are intended to be encompassed within the scope of the present invention.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology can exist as solvates, especially hydrates. Hydrates may form during manufacture of the compounds or compositions comprising the compounds, or hydrates may form over time due to the hygroscopic nature of the compounds. Compounds of the present technology can exist as organic solvates as well, including DMF, ether, and alcohol solvates among others.

The identification and preparation of any particular solvate is within the skill of the ordinary artisan of synthetic organic or medicinal chemistry.

Unless indicated otherwise, the nomenclature of substituents that are not explicitly defined herein are arrived at by naming the terminal portion of the functionality followed by the adjacent functionality toward the point of attachment.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and d or l enriched stereomeric mixtures, as well as the individual optical isomers can be isolated or synthesized so as to be substantially free of their enantiomeric or diastereomeric partners, and these stereoisomers are all within the scope of the present technology.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that each functional group is substituted (at from one to three positions) and that any and all of those substituent groups may be substituted one more time (at from one to three positions).

It is understood that the above definitions are not intended to include impermissible substitution patterns (e.g., methyl substituted with 5 fluoro groups). Such impermissible substitution patterns are well known to the skilled artisan.

Throughout this application, the text refers to various embodiments of the present compounds, compositions, and methods. The various embodiments described are meant to provide a variety of illustrative examples and should not be construed as descriptions of alternative species. Rather, it should be noted that the descriptions of various embodiments provided herein may be of overlapping scope. The embodiments discussed herein are merely illustrative and are not meant to limit the scope of the present technology.

Compounds

The present disclosure provides compounds that exhibit both hydrophobicity and a high affinity for calcium and other metals in mineralized forms, including biominerals. The compounds can be used in a variety of applications in which both hydrophobicity and binding to metal-containing materials are desired.

More specifically, in a first aspect, the present disclosure provides a compound of Formula IV Formula IV

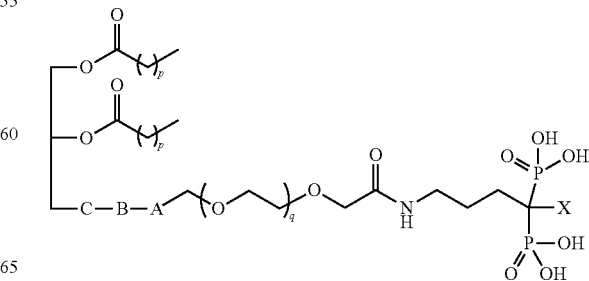

or a salt, isomer, or salt of an isomer thereof, wherein:

p is from 10 to 30;

q is from 1 to 100; C is selected from the group consisting of:

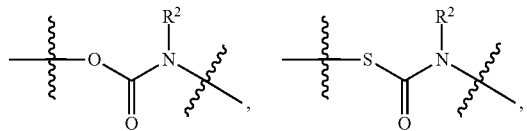
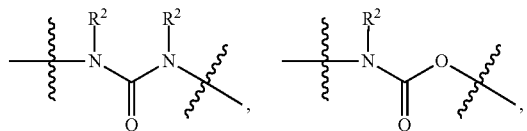
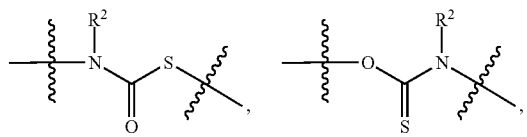
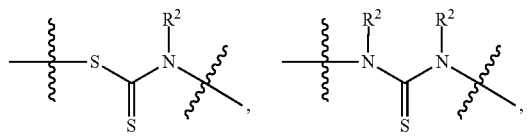
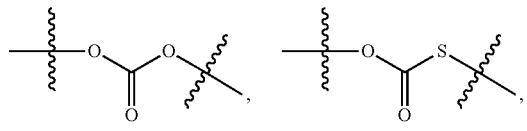
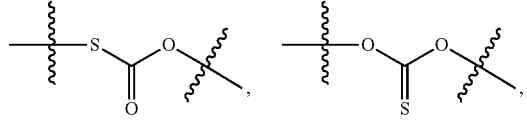
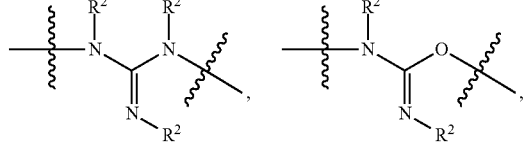

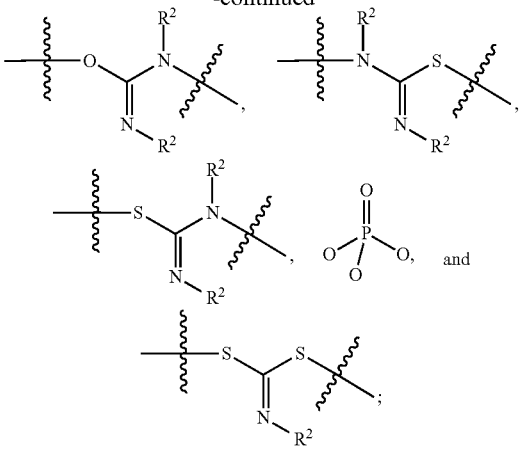

B is selected from the group consisting of: a covalent bond and an ethyl group;

A is selected from the group consisting of: a covalent bond, acyl, acylamino, aminoacyl, acyloxy, thioacyl, aminocarbonyl, aminoacyl carbonyloxy, aminothiocarbonyl, aminocarbonylamino, aminothiocarbonylamino, aminocarbonyloxy, aminosulfonyloxy, aminosulfonylamino, aminosulfonyl, amidino, and carboxy ester; and X is selected from the group consisting of: hydrogen, silyl, acyl, aminoacyl, thioacyl, aminocarbonyl, aminoacyl carbonyloxy, aminothiocarbonyl, aminosulfonyl, amidino, substituted sulfonyl, substituted sulfinyl, carboxy ester, phthalimido, OH, $SO_3H$ and $PO_3H$.

In some embodiments, p is from 12 to 28, from 14 to 26, from 14 to 24, from 14 to 22, from 14 to 20, from 16 to 20, or from 16 to 18. In some embodiments, p is 16. In some embodiments, q is from 1 to 100, from 5 to 90, from 10 to 80, from 15 to 70, from 20 to 60, from 25 to 50, from 30 to 50, from 40 to 50, or from 40 to 45. In some embodiments, q is 43. In some embodiments, q is 38, 39, 40, 41, 42, 43, 44, 45, 46, 47, 49, or 50. In some embodiments, C is

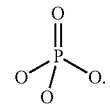

In some embodiments, the compound of Formula IV is a compound of Formula I

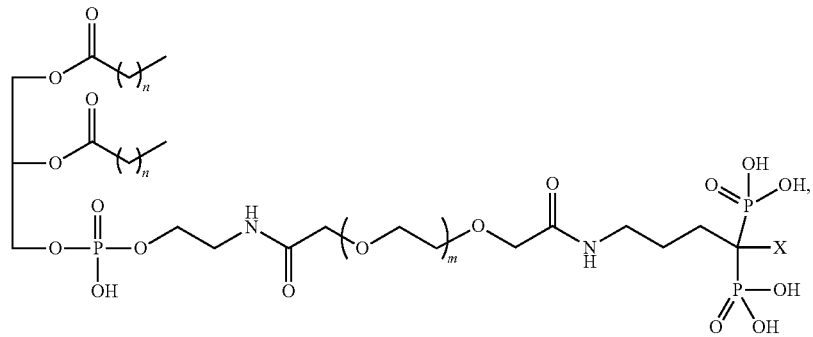

Formula I or a salt, isomer, or salt of an isomer thereof, wherein:
n is from 10 to 30,
m is from 1 to 100.

In some embodiments, n is from 20 to 25, from 12 to 20, from 14 to 18, or from 14 to 16. In some embodiments, n is 14 or 16. In some embodiments, m is from 1 to 90, from 5 to 80, from 10 to 70, from 20 to 60, from 30 to 50, or from 38 to 50. In some embodiments, m is 43. In some embodiments, q is 38, 39, 40, 41, 42, 43, 44, 45, 46, 47, 49, or 50. In some embodiments, X is selected from the group consisting of: hydrogen, silyl, acyl, aminoacyl, thioacyl, aminocarbonyl, aminoacyl carbonyloxy, aminothiocarbonyl, aminosulfonyl, amidino, substituted sulfonyl, substituted sulfinyl, carboxy ester, phthalimido, OH, SO$_3$H and PO$_3$H.

In some embodiments, the compound of Formula I is a compound of Formula Ia

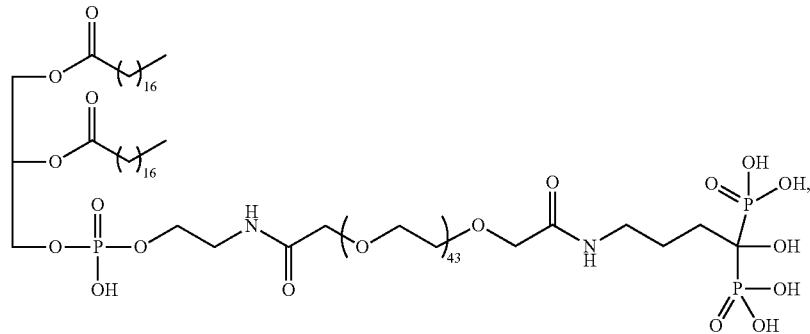

Formula Ia or a salt, isomer, or salt of an isomer thereof.

In some embodiments, the compound of Formula I is a compound of Formula Ib

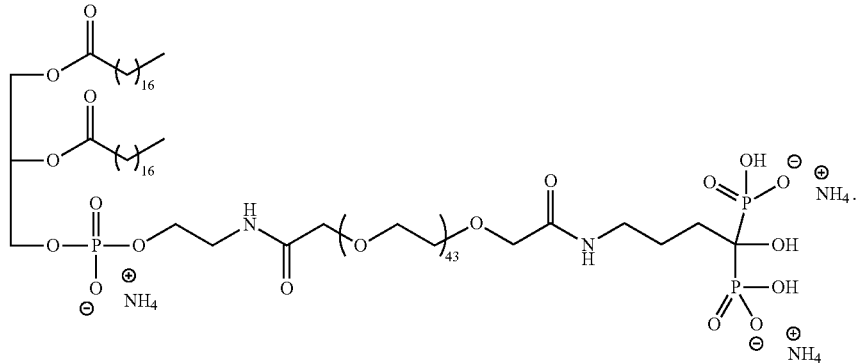

Formula Ib

Pharmaceutical Compositions

In a second aspect, the present disclosure provides for a pharmaceutical composition comprising
a compound of Formula IV

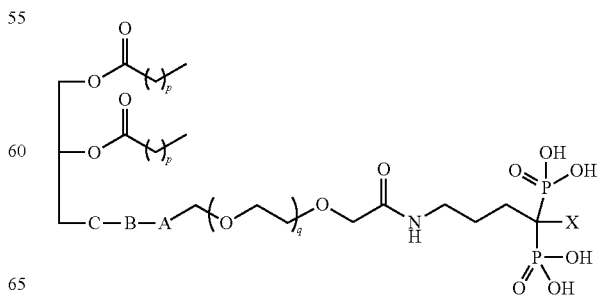

Formula IV or a pharmaceutically acceptable salt, isomer, or salt of an isomer thereof, wherein:

p is from 10 to 30;
q is from 1 to 100;
C is selected from the group consisting of:

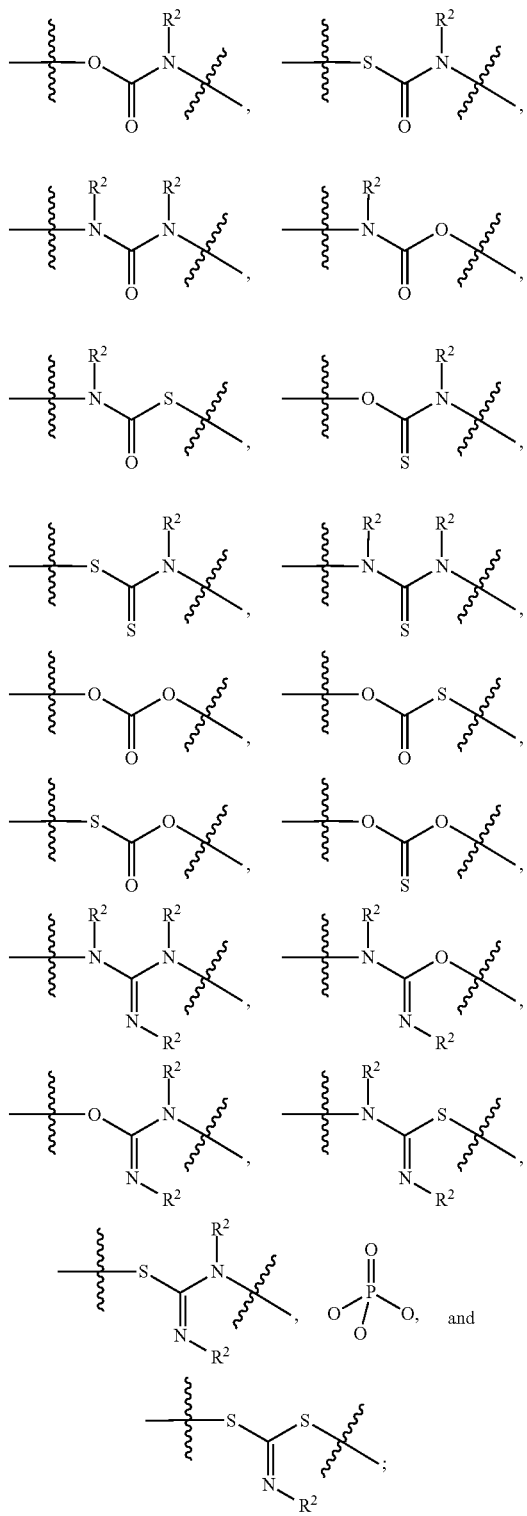

B is selected from the group consisting of: a covalent bond and an ethyl group;

A is selected from the group consisting of: a covalent bond, acyl, acylamino, aminoacyl, acyloxy, thioacyl, aminocarbonyl, aminoacyl carbonyloxy, aminothiocarbonyl, aminocarbonylamino, aminothiocarbonylamino, aminocarbonyloxy, aminosulfonyloxy, aminosulfonylamino, aminosulfonyl, amidino, and carboxy ester; and X is selected from the group consisting of: hydrogen, silyl, acyl, aminoacyl, thioacyl, aminocarbonyl, aminoacyl carbonyloxy, aminothiocarbonyl, aminosulfonyl, amidino, substituted sulfonyl, substituted sulfinyl, carboxy ester, phthalimido, $SO_3H$ and $PO_3H$; and optionally, a pharmaceutically acceptable excipient or diluent In some embodiments, p is from 12 to 28, from 14 to 26, from 14 to 24, from 14 to 22, from 14 to 20, from 16 to 20, or from 16 to 18. In some embodiments, p in the pharmaceutical composition is 10, 11, 12, 13, 14, 15, 16, 17, 18, 19, or 20. In some embodiments, an average value of p in the pharmaceutical composition is from 12 to 28, from 14 to 26, from 14 to 24, from 14 to 22, from 14 to 20, from 16 to 20, or from 16 to 18. In some embodiments, an average value of p in the pharmaceutical composition is 10, 11, 12, 13, 14, 15, 16, 17, 18, 19, or 20.

In some embodiments, q is from 1 to 100, from 5 to 90, from 10 to 80, from 15 to 70, from 20 to 60, from 25 to 50, from 30 to 50, from 40 to 50, or from 40 to 45. In some embodiments, q is 43. In some embodiments, q is 38, 39, 40, 41, 42, 43, 44, 45, 46, 47, 49, or 50. In some embodiments, an average value of q in the pharmaceutical composition is from 1 to 100, from 5 to 90, from 10 to 80, from 15 to 70, from 20 to 60, from 25 to 50, from 30 to 50, from 40 to 50, or from 40 to 45. In some embodiments, an average value of q in the pharmaceutical composition is 38, 39, 40, 41, 42, 43, 44, 45, 46, 47, 49, or 50.

In some embodiments of the pharmaceutical composition, molecular weight of the compound of Formula IV is 1,500 to 5,000 Daltons. In certain embodiments, the molecular weight of the compound of Formula IV is 1,500 to 5,000 Daltons. In certain embodiments, the molecular weight of the compound of Formula IV is 2,000 to 4,500 Daltons. In certain embodiments, the molecular weight of the compound of Formula IV is 2,500 to 4,000 Daltons. In certain embodiments, the molecular weight of the compound of Formula IV is 3,000 to 3,500 Daltons In some embodiments, C is

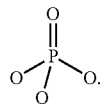

In some embodiments of the pharmaceutical composition, the compound of Formula IV is a compound of Formula I

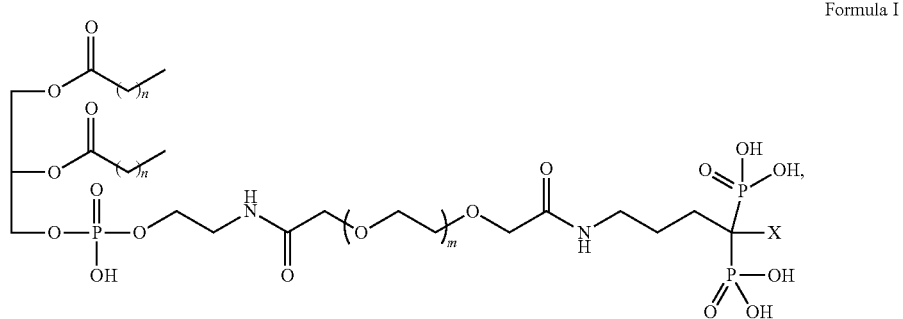

Formula I or a salt, isomer, or salt of an isomer thereof, wherein:
n is from 10 to 30 and
m is from 1 to 100.

In some embodiments, n is from 10 to 50, from 20 to 25, from 12 to 20, from 14 to 18, or from 14 to 16. In some embodiments, n is 14 or 16. In some embodiments, n is 10, 11, 12, 13, 14, 15, 16, 17, 18, 19, or 20. In some embodiments, an average value of n in the pharmaceutical composition is from 10 to 50, from 20 to 25, from 12 to 20, from 14 to 18, or from 14 to 16. In some embodiments, an average value of n in the pharmaceutical composition is 14 or 16. In some embodiments, an average value of n in the pharmaceutical composition is 10, 11, 12, 13, 14, 15, 16, 17, 18, 19, or 20.

In some embodiments, m is from 1 to 150, from 1 to 140, from 1 to 130, from 1 to 120, 1 to 110, from 1 to 100, from 1 to 90, from 5 to 80, from 10 to 70, from 20 to 60, from 30 to 50, or from 38 to 50. In some embodiments, m is 43. In some embodiments, m is 38, 39, 40, 41, 42, 43, 44, 45, 46, 47, 49, or 50. In some embodiments, an average value of m in the pharmaceutical composition is from 1 to 150, from 1 to 140, from 1 to 130, from 1 to 120, 1 to 110, from 1 to 100, from 1 to 90, from 5 to 80, from 10 to 70, from 20 to 60, from 30 to 50, or from 38 to 50. In some embodiments, an average value of m in the pharmaceutical composition is 43. In some embodiments, an average value of m in the pharmaceutical composition is 38, 39, 40, 41, 42, 43, 44, 45, 46, 47, 49, or 50.

In some embodiments of the pharmaceutical composition, the molecular weight of the compound of Formula I is 1,500 to 5,000 Daltons. In certain embodiments, the molecular weight of the compound of Formula I is 2,000 to 4,500 Daltons. In certain embodiments, the molecular weight of the compound of Formula I is 2,500 to 4,000 Daltons. In certain embodiments, the molecular weight of the compound of Formula I is 3,000 to 3,500 Daltons.

In some embodiments, X is selected from the group consisting of: hydrogen, silyl, acyl, aminoacyl, thioacyl, aminocarbonyl, aminoacyl carbonyloxy, aminothiocarbonyl, aminosulfonyl, amidino, substituted sulfonyl, substituted sulfinyl, carboxy ester, phthalimido, OH, $SO_3H$ and $PO_3H$.

In some embodiments, the compound of Formula I is a compound of Formula Ia

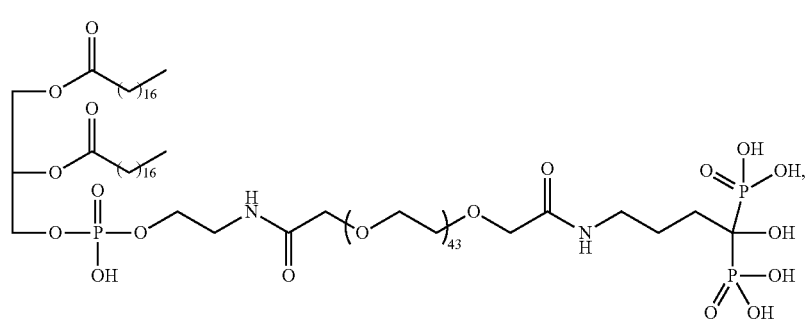

Formula Ia or a salt, isomer or salt of an isomer thereof.

In some embodiments of the pharmaceutical composition, the average molecular weight of the compound of Formula Ia is about 3500 Daltons. In some embodiments, the average molecular weight of the compound of Formula Ia is about 3200 Daltons. In some embodiments, the average molecular weight of the compound of Formula Ia is about 2500 Daltons. In some embodiments, the average molecular weight of the compound of Formula Ia is about 2000 Daltons.

In some embodiments of the pharmaceutical composition, the compound of Formula Ia is the compound of Formula Ib Formula Ib

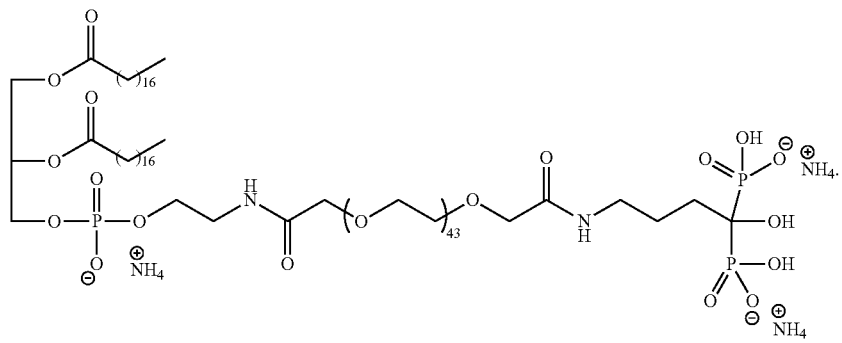

In some embodiments, the compound of Formula I is the compound of Formula Ib

Formula Ib

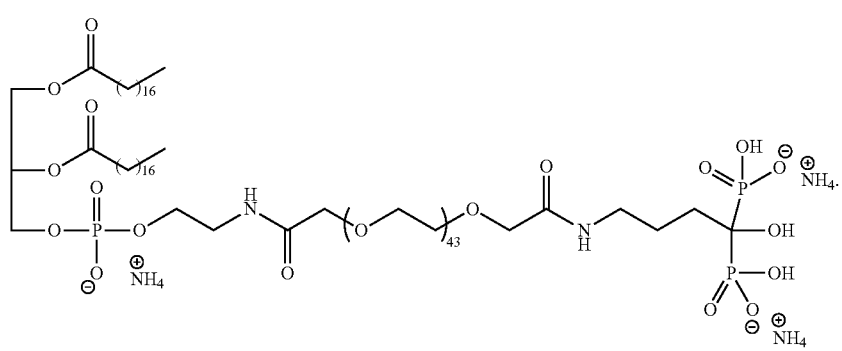

In some embodiments of the pharmaceutical composition, the average molecular weight of the compound of Formula Ib is about 3500 Daltons. In some embodiments, the average molecular weight of the compound of Formula Ib is about 3200 Daltons. In some embodiments, the average molecular weight of the compound of Formula Ib is about 2500 Daltons. In some embodiments, the average molecular weight of the compound of Formula Ib is about 2000 Daltons.

In some embodiments, chain lengths (16 and 43) in Formula Ib is an average chain length of the compound in the pharmaceutical composition.

In some embodiments of the pharmaceutical composition, the composition further comprises at least one additional phospholipid compound.

In some embodiments, the pharmaceutical composition further comprises
a compound of Formula II Formula II

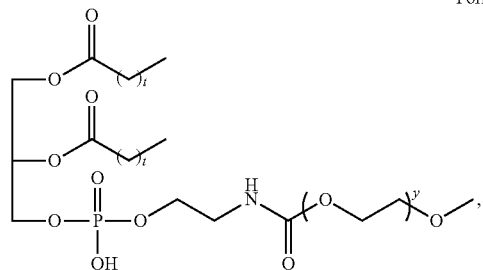

or a pharmaceutically acceptable salt or isomer thereof.

In some embodiments, t is from 10 to 30, from 12 to 28, from 14 to 25, from 16 to 22, from 16 to 20, or from 18 to 20. In some embodiments, t is 14 or 16. In some embodiments, an average value of t in the pharmaceutical composition is from 10 to 30, from 12 to 28, from 14 to 25, from 16 to 22, from 16 to 20, or from 18 to 20. In some embodiments, an average value of t in the pharmaceutical composition is 14 or 16.

In some embodiments, y is from 1-100, from 5 to 90, from 10 to 80, from 20 to 70, from 40 to 60, or from 40 to 50. In some embodiments, y is from 38 to 50. In some embodiments, an average value of y in the pharmaceutical composition is from 1-100, from 5 to 90, from 10 to 80, from 20 to 70, from 40 to 60, or from 40 to 50. In some embodiments, an average value of y in the pharmaceutical composition is from 38 to 50.

In some embodiments of the pharmaceutical composition, the molecular weight of the compound of Formula II is 1,500 to 5,000 Daltons. In certain embodiments, the molecular weight of the compound of Formula II is 2,000 to 4,500 Daltons. In certain embodiments, the molecular weight of the compound of Formula II is 2,500 to 4,000 Daltons. In particular embodiments, the molecular weight of the compound of Formula II is 3,000 to 3,500 Daltons.

In some embodiments of the pharmaceutical composition, the compound of Formula II is a compound of Formula IIa Formula IIa

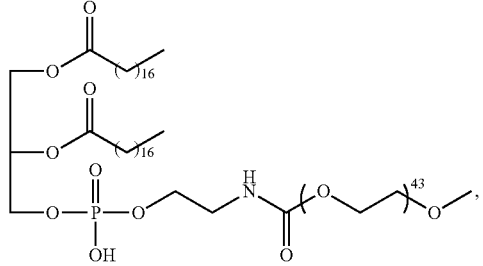

or a pharmaceutically acceptable salt or isomer thereof.

In some embodiments of the pharmaceutical composition, the average molecular weight of the compound of Formula IIa is about 3000 Daltons. In some embodiments, the average molecular weight of the compound of Formula IIa is about 2800 Daltons. In some embodiments, the average molecular weight of the compound of Formula IIa is about 2600 Daltons. In some embodiments, the average molecular weight of the compound of Formula IIa is about 2400 Daltons. In some embodiments, the average molecular weight of the compound of Formula IIa is about 2200 Daltons. In some embodiments, the average molecular weight of the compound of Formula IIa is about 2000 Daltons.

In some embodiments, chain lengths (16 and 43) in Formula IIa is an average chain length of the compound in the pharmaceutical composition.

In some embodiments of the pharmaceutical composition, the compound of Formula II is the compound of Formula IIIb Formula IIb

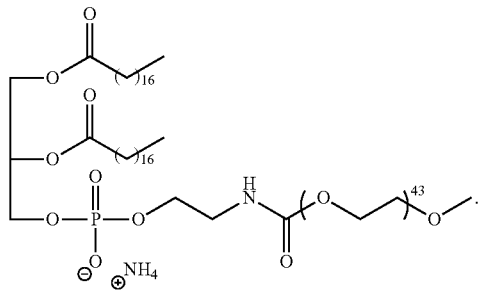

In some embodiments of the pharmaceutical composition, the average molecular weight of the compound of Formula IIb is about 3000 Daltons. In some embodiments, the average molecular weight of the compound of Formula IIb is about 2800 Daltons. In some embodiments, the average molecular weight of the compound of Formula I % is about 2600 Daltons. In some embodiments, the average molecular weight of the compound of Formula IIb is about 2400 Daltons. In some embodiments, the average molecular weight of the compound of Formula IIb is about 2200 Daltons. In some embodiments, the average molecular weight of the compound of Formula IIb is about 2000 Daltons.

In some embodiments, chain lengths (16 and 43) in Formula IIb is an average chain length of the compound in the pharmaceutical composition.

In some embodiments, the pharmaceutical composition further comprises
a compound of Formula III Formula III

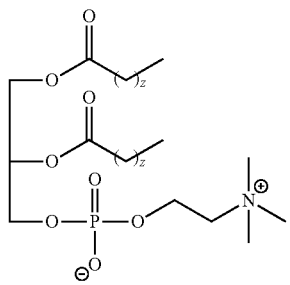

or a pharmaceutically acceptable salt or isomer thereof. In some embodiments, z is from 10 to 30, from 10 to 25, from 12 to 20, from 15 to 20, or from 16 to 18. In some embodiments, z is 14 or 16. In some embodiments, an average value of z in the pharmaceutical composition is from 10 to 30, from 10 to 25, from 12 to 20, from 15 to 20, or from 16 to 18. In some embodiments, an average value of z in the pharmaceutical composition is 14 or 16.

In some embodiments of the pharmaceutical composition, the molecular weight of the compound of Formula III is 500 to 2,000 Daltons. In certain embodiments, the molecular weight of the compound of Formula III is 750 to 1,750 Daltons. In certain embodiments, the molecular weight of the compound of Formula III is 1,000 to 1,500 Daltons. In certain embodiments, the molecular weight of the compound of Formula III is 1,100 to 1,400 Daltons. In certain embodiments, the molecular weight of the compound of Formula III is 1200 to 1,300 Daltons.

In some embodiments of the pharmaceutical composition, the compound of Formula III is the compound of Formula IIIa Formula IIIa

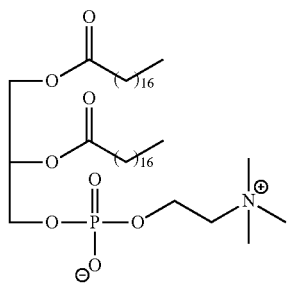

In some embodiments of the pharmaceutical composition, the average molecular weight of the compound of Formula IIIa is about 840 Daltons. In some embodiments, the average molecular weight of the compound of Formula IIIa is about 790 Daltons. In some embodiments, the average molecular weight of the compound of Formula IIIa is about 750 Daltons. In some embodiments, the average molecular weight of the compound of Formula IIIa is about 700

Daltons. In some embodiments, the average molecular weight of the compound of Formula IIIa is about 650 Daltons.

In some embodiments, the chain length (16) in Formula IIIa is an average chain length of the compound in the pharmaceutical composition.

In some embodiments, the pharmaceutical composition comprises no more than 5 mol % of the compound of Formula IV or a salt thereof. Mol % as used herein refers to a percentage of the number of molecules of a given lipid compound (e.g., the compound of Formula IV, Formula I, Formula II, Formula III, or a salt, isomer, or salt of an isomer thereof) over total number of molecules of all lipid compounds within the pharmaceutical composition. Similarly, in the context of microspheres, mol % as used herein refers to a percentage of the number of molecules of a given lipid compound (e.g., the compound of Formula IV, Formula I, Formula II, Formula III, or a salt, isomer, salt of an isomer thereof) over total number of molecules of all lipid compounds within the microspheres. In certain embodiments, the pharmaceutical composition comprises no more than 4 mol % of the compound of Formula IV or a salt thereof. In certain embodiments, the pharmaceutical composition comprises no more than 4 mol % of the compound of Formula IV or a salt thereof. In certain embodiments, the pharmaceutical composition comprises no more than 3 mol % of the compound of Formula IV or a salt thereof. In certain embodiments, the pharmaceutical composition comprises no more than 2 mol % of the compound of Formula IV or a salt thereof. In certain embodiments, the pharmaceutical composition comprises no more than 1 mol % of the compound of Formula IV or a salt thereof.

In some embodiments, the pharmaceutical composition comprises 0.1-5 mol % of the compound of Formula IV or a salt thereof. In some embodiments, the pharmaceutical composition comprises 0.1-10, 0.1-5, 0.5-5, 1-5, 1-4, 1-3, 2-3, 2-4, or 3-5 mol % of the compound of Formula IV or a salt thereof.

In some embodiments, the composition comprises 0.01-5 mol % of the compound of Formula I, or a salt thereof. In certain embodiments, the composition comprises 0.1-5 mol % of the compound of Formula I, or a salt thereof. In some embodiments, the pharmaceutical composition comprises 0.1-10, 0.1-5, 0.5-5, 1-5, 1-4, 1-3, 2-3, 2-4, or 3-5 mol % of the compound of Formula I or a salt thereof.

In some embodiments, the pharmaceutical composition comprises no more than 5 mol % of the compound of Formula I or a salt thereof. In certain embodiments, the pharmaceutical composition comprises no more than 4 mol % of the compound of Formula I or a salt thereof. In certain embodiments, the pharmaceutical composition comprises no more than 3 mol % of the compound of Formula I or a salt thereof. In certain embodiments, the pharmaceutical composition comprises no more than 2 mol % of the compound of Formula I or a salt thereof. In certain embodiments, the pharmaceutical composition comprises no more than 1 mol % of the compound of Formula I or a salt thereof.

In some embodiments, the pharmaceutical composition comprises 0.01-5 mol % of a compound of Formula Ia or Ib. In certain embodiments, the pharmaceutical composition comprises 0.1-5 mol % of a compound of Formula Ia or Ib. In certain embodiments, the composition comprises 0.5-4.5 mol % of a compound of Formula Ia or Ib. In certain embodiments, the composition comprises 1.0-4.0 mol % of a compound of Formula Ia or Ib. In certain embodiments, the composition comprises 1.5-3.5 mol % of a compound of Formula Ia or Ib. In certain embodiments, the composition comprises 2.0-3.0 mol % of a compound of Formula Ia or Ib.

In some embodiments, the composition comprises no more than 5 mol % of a compound of Formula Ia or Ib. In some embodiments, the composition comprises no more than 4.5 mol % of a compound of Formula Ia or Ib. In some embodiments, the composition comprises no more than 4.0 mol % of a compound of Formula Ia or Ib. In some embodiments, the composition comprises no more than 3.5 mol % of a compound of Formula Ia or Ib. In some embodiments, the composition comprises no more than 3.0 mol % of a compound of Formula Ia or Ib. In some embodiments, the composition comprises no more than 2.5 mol % of a compound of Formula Ia or Ib. In some embodiments, the composition comprises no more than 2.0 mol % of a compound of Formula Ia or Ib. In some embodiments, the composition comprises no more than 1.5 mol % of a compound of Formula Ia or Ib. In some embodiments, the composition comprises no more than 1.0 mol % of a compound of Formula Ia or Ib. In some embodiments, the composition comprises no more than 0.5 mol % of a compound of Formula Ia or Ib. In some embodiments, the composition comprises no more than 0.1 mol % of a compound of Formula Ia or Ib. In some embodiments, the composition comprises no more than 0.05 mol % of a compound of Formula Ia or Ib.

In some embodiments, the composition comprises 5-10 mol % of the compound of Formula II, or a salt thereof.

In some embodiments, the pharmaceutical composition comprises no more than 10 mol % of the compound of Formula II or a salt thereof. In certain embodiments, the pharmaceutical composition comprises no more than 8 mol % of the compound of Formula II or a salt thereof. In certain embodiments, the composition comprises no more than 6 mol % of the compound of Formula II or a salt thereof. In certain embodiments, the pharmaceutical composition comprises no more than 4 mol % of the compound of Formula II or a salt thereof. In certain embodiments, the pharmaceutical composition comprises no more than 3 mol % of the compound of Formula II or a salt thereof. In certain embodiments, the pharmaceutical composition comprises no more than 2 mol % of the compound of Formula II or a salt thereof. In certain embodiments, the pharmaceutical composition comprises no more than 1 mol % of the compound of Formula II or a salt thereof.

In some embodiments, the pharmaceutical composition comprises 5-10 mol % of the compound of Formula II or a salt thereof. In some embodiments, the pharmaceutical composition comprises 5-20, 5-15, 5-10, 5-9.9, 5-9.6, 5-9, 5-9, 7-9, or 8-9 mol % of the compound of Formula II or a salt thereof.

In some embodiments, the composition comprises 5.0-10.0 mol % of a compound of Formula IIa or IIb. In certain embodiments, the composition comprises 5.5-9.5 mol % of a compound of Formula IIa or IIb. In certain embodiments, the composition comprises 6.0-9.0 mol % of a compound of Formula IIa or IIb. In certain embodiments, the composition comprises 6.5-8.5 mol % of a compound of Formula IIa or IIb. In certain embodiments, the composition comprises 7.0-8.0 mol % of a compound of Formula IIa or ill).

In some embodiments, the composition comprises no more than 10 mol % of a compound of Formula IIa or IIb. In some embodiments, the composition comprises no more than 9.5 mol % of a compound of Formula IIa or IIb. In some embodiments, the composition comprises no more than 9.0 mol % of a compound of Formula IIa or IIb. In some embodiments, the composition comprises no more than 8.5 mol % of a compound of Formula IIa or IIb. In some embodiments, the composition comprises no more than 8.0 mol % of a compound of Formula IIa or IIb. In some embodiments, the composition comprises no more than 7.5 mol % of a compound of Formula IIa or IIb. In some embodiments, the composition comprises no more than 7.0 mol % of a compound of Formula IIa or IIb. In some embodiments, the composition comprises no more than 6.5 mol % of a compound of Formula IIa or IIb. In some embodiments, the composition comprises no more than 6.0 mol % of a compound of Formula IIa or IIb. In some embodiments, the composition comprises no more than 5.5 mol % of a compound of Formula IIa or IIb. In some embodiments, the composition comprises no more than 5.0 mol % of a compound of Formula IIa or IIb.

In some embodiments, the composition comprises 80-95 mol % of the compound of Formula III, or a salt thereof. In some embodiments, the pharmaceutical composition comprises 70-99, 75-98, 75-97, 80-95 mol % of the compound of Formula III or a salt thereof.

In some embodiments, the pharmaceutical composition comprises no more than 95 mol % of the compound of Formula III or a salt thereof. In certain embodiments, the pharmaceutical composition comprises no more than 85 mol % of the compound of Formula III or a salt thereof. In certain embodiments, the pharmaceutical composition comprises no more than 75 mol % of the compound of Formula III or a salt thereof. In certain embodiments, the pharmaceutical composition comprises no more than 65 mol % of the compound of Formula III or a salt thereof. In certain embodiments, the pharmaceutical composition comprises no more than 55 mol % of the compound of Formula III or a salt thereof. In certain embodiments, the pharmaceutical composition comprises no more than 45 mol % of the compound of Formula III or a salt thereof. In certain embodiments, the pharmaceutical composition comprises no more than 35 mol % of the compound of Formula III or a salt thereof. In certain embodiments, the pharmaceutical composition comprises no more than 25 mol % of the compound of Formula III or a salt thereof. In certain embodiments, the pharmaceutical composition comprises no more than 15 mol % of the compound of Formula III or a salt thereof. In certain embodiments, the pharmaceutical composition comprises no more than 5 mol % of the compound of Formula III or a salt thereof.

In some embodiments, the composition comprises 80-95 mol % of the compound of Formula IIIa. In certain embodiments, the composition comprises 82.5-92.5 mol % of the compound of Formula IIIa. In certain embodiments, the composition comprises 85-90 mol % of the compound of Formula IIIa. In certain embodiments, the composition comprises 87.5-92.5 mol % of the compound of Formula IIIa.

In some embodiments of the pharmaceutical composition, the molar ratio of the compound of Formula IV to the compound of Formula II ranges from 1:1000 to 1:1. In certain embodiments of the pharmaceutical composition, the molar ratio of the compound of Formula IV to the compound of Formula II ranges from 1:500 to 1:1. In certain embodiments of the pharmaceutical composition, the molar ratio of the compound of Formula IV to the compound of Formula II ranges from 1:100 to 1:1. In certain embodiments, the molar ratio of the compound of Formula IV to the compound of Formula II ranges from 1:90 to 1:5. In certain embodiments, the molar ratio of the compound of Formula IV to the compound of Formula II ranges from 1:80 to 1:10. In certain embodiments, the molar ratio of the compound of Formula IV to the compound of Formula II ranges from 1:70 to 1:20. In certain embodiments, the molar ratio of the compound of Formula IV to the compound of Formula II ranges from 1:60 to 1:30. In certain embodiments, the molar ratio of the compound of Formula IV to the compound of Formula II ranges from 1:50 to 1:40.

In some embodiments of the pharmaceutical composition, the molar ratio of the compound of Formula I to the compound of Formula II ranges from 1:1000 to 1:1. In certain embodiments of the pharmaceutical composition, the molar ratio of the compound of Formula I to the compound of Formula II ranges from 1:500 to 1:1. In certain embodiments of the pharmaceutical composition, the molar ratio of the compound of Formula I to the compound of Formula II ranges from 1:100 to 1:1. In certain embodiments, the molar ratio of the compound of Formula I to the compound of Formula II ranges from 1:90 to 1:5. In certain embodiments, the molar ratio of the compound of Formula I to the compound of Formula II ranges from 1:80 to 1:10. In certain embodiments, the molar ratio of the compound of Formula I to the compound of Formula II ranges from 1:70 to 1:20. In certain embodiments, the molar ratio of the compound of Formula I to the compound of Formula II ranges from 1:60 to 1:30. In certain embodiments, the molar ratio of the compound of Formula I to the compound of Formula II ranges from 1:50 to 1:40.

In some embodiments of the pharmaceutical composition, the molar ratio of the compound of Formula Ia to the compound of Formula IIa ranges from 1:1000 to 1:1. In some embodiments of the pharmaceutical composition, the molar ratio of the compound of Formula Ia to the compound of Formula IIa ranges from 1:500 to 1:1. In some embodiments of the pharmaceutical composition, the molar ratio of the compound of Formula Ia to the compound of Formula IIa ranges from 1:100 to 1:1. In some embodiments, the molar ratio of the compound of Formula Ia to the compound of Formula IIa ranges from 1:90 to 1:5. In some embodiments, the molar ratio of the compound of Formula Ia to the compound of Formula IIa ranges from 1:80 to 1:10. In some embodiments, the molar ratio of the compound of Formula Ia to the compound of Formula IIa ranges from 1:70 to 1:20. In some embodiments, the molar ratio of the compound of Formula Ia to the compound of Formula IIa ranges from 1:60 to 1:30. In some embodiments, the molar ratio of the compound of Formula Ia to the compound of Formula IIa ranges from 1:50 to 1:40.

In some embodiments of the pharmaceutical composition, the molar ratio of the compound of Formula Ib to the compound of Formula IIb ranges from 1:1000 to 1:1. In some embodiments of the pharmaceutical composition, the molar ratio of the compound of Formula Ib to the compound of Formula IIb ranges from 1:500 to 1:1. In some embodiments of the pharmaceutical composition, the molar ratio of the compound of Formula Ib to the compound of Formula IIb ranges from 1:100 to 1:1. In some embodiments, the molar ratio of the compound of Formula Ib to the compound of Formula IIb ranges from 1:90 to 1:5. In some embodiments, the molar ratio of the compound of Formula Ib to the compound of Formula IIb ranges from 1:80 to 1:10. In some embodiments, the molar ratio of the compound of Formula Ib to the compound of Formula IIb ranges from 1:70 to 1:20. In some embodiments, the molar ratio of the compound of Formula Ib to the compound of Formula IIb ranges from 1:60 to 1:30. In some embodiments, the molar ratio of the compound of Formula Ib to the compound of Formula IIb ranges from 1:50 to 1:40.

In some embodiments of the pharmaceutical composition, the molar ratio of the compound of Formula II to the compound of Formula III ranges from 1:20 to 1:8. In certain embodiments, the molar ratio of the compound of Formula II to the compound of Formula III ranges from 1:18 to 1:10. In certain embodiments, the molar ratio of the compound of Formula II to the compound of Formula III ranges from 1:16 to 1:12. In certain embodiments, the molar ratio of the compound of Formula II to the compound of Formula III ranges from 1:15 to 1:13.

In some embodiments of the pharmaceutical composition, the molar ratio of the compound of Formula IIa to the compound of Formula IIIa ranges from 1:20 to 1:8. In some embodiments, the molar ratio of the compound of Formula IIa to the compound of Formula IIIa ranges from 1:18 to 1:10. In some embodiments, the molar ratio of the compound of Formula IIa to the compound of Formula IIIa ranges from 1:16 to 1:12. In some embodiments, the molar ratio of the compound of Formula IIa to the compound of Formula IIIa ranges from 1:15 to 1:13.

In some embodiments of the pharmaceutical composition, the molar ratio of the compound of Formula IIb to the compound of Formula IIIa ranges from 1:20 to 1:8. In some embodiments, the molar ratio of the compound of Formula IIb to the compound of Formula IIIa ranges from 1:18 to 1:10. In some embodiments, the molar ratio of the compound of Formula IIb to the compound of Formula IIIa ranges from 1:16 to 1:12. In some embodiments, the molar ratio of the compound of Formula IIb to the compound of Formula IIIa ranges from 1:15 to 1:13.

In some embodiments, the pharmaceutical composition comprises a compound of Formula IV, optionally as Formula I, or a pharmaceutically acceptable salt, isomer, or salt of an isomer thereof a compound of Formula II or a pharmaceutically acceptable salt, isomer, or salt of an isomer thereof; and a compound of Formula III or a pharmaceutically acceptable salt, isomer, or salt of an isomer thereof.

In some embodiments, the pharmaceutical composition comprises the ammonium salt of at least one of the compounds of Formula IV, Formula I, Formula II, and Formula III.

In some embodiments, the pharmaceutical composition comprises a homogenous population of a compound having identical carbon chain lengths. In some embodiments, the pharmaceutical composition comprises a heterogenous population of a lipid compound having various lengths for each carbon chain. In such embodiments, chain lengths represented as a variable or a specific number in Formula IV, Formula I, Formula Ia, Formula Ib, Formula II, Formula IIa, Formula IIb, Formula III, or Formula IIIa refer to an average number of chain links of the lipid composition present in the pharmaceutical composition.

In some embodiments, the composition further comprises a fluid with a normal boiling point less than 30° C.

In typical embodiments, the fluid is a gas at the temperatures and pressures present in the mammalian urinary tract. In preferred embodiments, the fluid is responsive to energy of various forms, such as electromagnetic energy, acoustic energy, microwave energy, photonic energy, or others. In certain embodiments, the fluid has low solubility in aqueous solutions, and is air, nitrogen, argon, $CO_2$, sulfur hexafluoride, a fluorinated $C_{1-6}$ alkane, or a combination thereof.

In some embodiments of the pharmaceutical composition, the fluid is a perfluorocarbon. In some embodiments, the fluid is selected from octafluoropropane, n-decafluorobutane, n-perfluoropropane, tetradecafluorohexane, and dodecafluoropentane. In a particular embodiment, the fluid is n-decafluorobtuane (a.k.a., perfluorobutane).

In some embodiments of the pharmaceutical composition, the compound of formula IV, which in typical embodiments is a compound of formula I; the compound of formula II; the compound of formula III; and the liquid with a normal boiling point less than 30° C. are capable of assembling into microspheres. Thus, in some embodiments, the pharmaceutical composition comprises microspheres, the microspheres comprising a lipid shell surrounding a fluid with normal boiling point less than 30° C., wherein the lipid shell comprises compounds of formulae I, II and III.

A mean diameter of the microspheres can be measured using any of the methods known in the art. In some embodiments, the mean diameter is measured by electro-zone sensing, for example using a Coulter counter. In some embodiments, the microspheres have a mean diameter of about 0.1 micron to about 10 microns, or 0.1 microns to 10 microns when measured by electro-zone sensing. In certain embodiments, the microspheres have a mean diameter of about 0.2 micron to about 9.5 microns. In certain embodiments, the microspheres have a mean diameter of about 0.3 micron to about 9.0 microns. In certain embodiments, the microspheres have a mean diameter of about 0.5 micron to about 8.5 microns. In certain embodiments, the microspheres have a mean diameter of about 0.5 micron to about 8.0 microns. In certain embodiments, the microspheres have a mean diameter of about 0.5 micron to about 7.5 microns. In certain embodiments, the microspheres have a mean diameter of about 0.5 micron to about 7.0 microns. In certain embodiments, the microspheres have a mean diameter of about 0.5 micron to about 6.5 microns. In certain embodiments, the microspheres have a mean diameter of about 0.5 micron to about 6.0 microns. In certain embodiments, the microspheres have a mean diameter of about 0.5 micron to about 5.5 microns. In certain embodiments, the microspheres have a mean diameter of about 0.5 micron to about 5 microns. In certain embodiments, the microspheres have a mean diameter of about 0.5 micron to about 4 microns. In certain embodiments, the microspheres have a mean diameter of about 0.5 micron to about 3 microns. In certain embodiments, the microspheres have a mean diameter of about 0.5 micron to about 2 microns. In certain embodiments, the microspheres have a mean diameter of about 0.5 micron, 0.6 micron, 0.7 micron, 0.8 micron, 0.9 micron, 1 micron, or 5 microns.

In some embodiments, the pharmaceutical composition comprising microspheres is a lyophilized powder or dry concentrate.

In other embodiments, the pharmaceutical composition comprising microspheres further comprises an aqueous medium, such as water, saline, or a buffered salt solution. In certain embodiments, the pharmaceutical composition comprises a phosphate buffered solution lacking calcium and magnesium ions. In particular embodiments, the composition further comprises phosphate buffered saline.

In some embodiments, the pharmaceutical composition comprising microspheres, whether lyophilized, dry concentrate, or liquid formulation, further comprises one or more of trehalose and PLASDONE K12 as excipients. PLASDONE K12 is a commercially available and product.

Method of Manufacturing Bisphosphonate-PEG-Lipid Compounds

In another aspect, the present disclosure provides methods of making bisphosphonate-PEG-lipid compounds.

Figure 2:
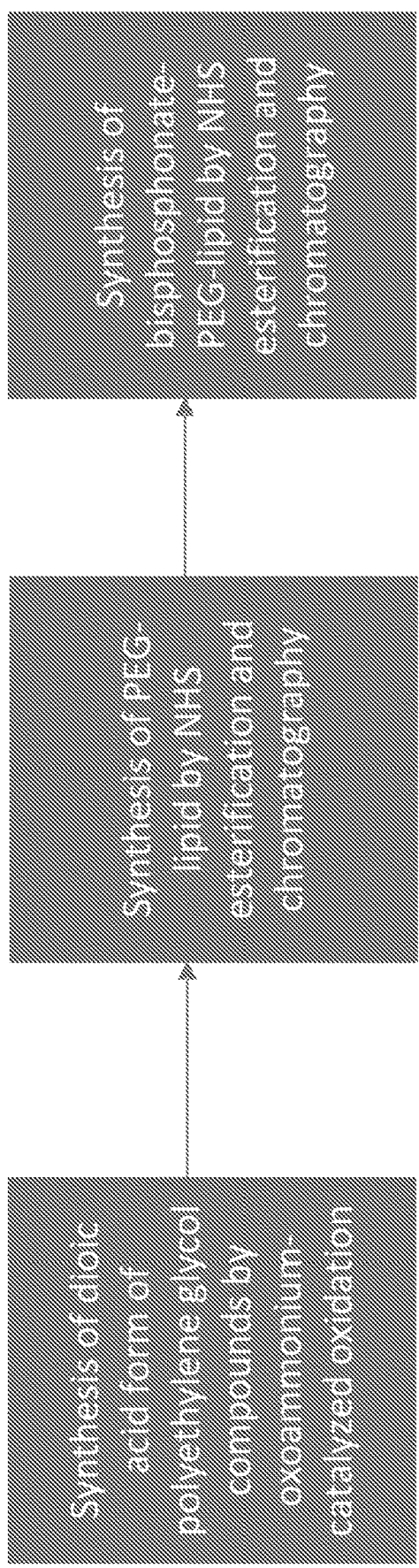
FIG. 2 is a block diagram illustrating exemplary steps of synthesizing a bisphosphonate-PEG-lipid provided in this disclosure.
Figure 3:
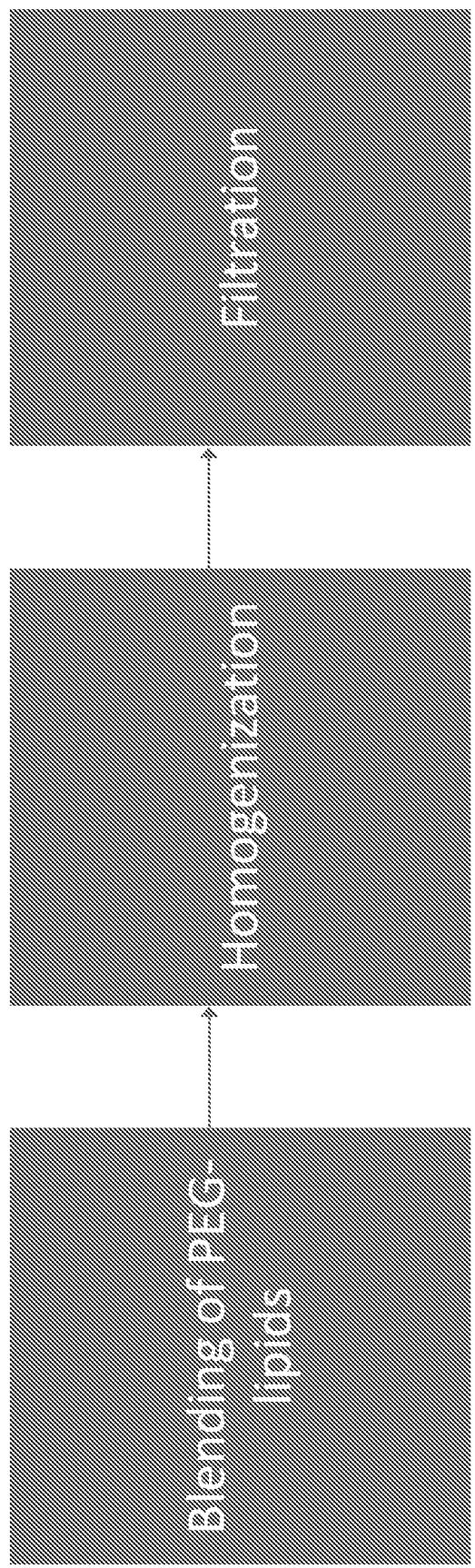
FIG. 3 is a block diagram illustrating exemplary steps of preparing a bisphosphonate-PEG-lipid for generating microspheres provided in this disclosure.

An exemplary method of making bisphosphonate-PEG-lipid compounds is illustrated in FIG. 2. The method comprises the steps of (i) synthesizing dioic acid form of polyethylene glycol compounds by oxoammonium-catalyzed oxidation; (ii) synthesizing PEG-lipid by NHS esterification and chromatography; and (iii) synthesizing bisphosphonate-PEG-lipid by NHS esterification and chromatography.

In a first step, the synthesis method comprises an oxidation reaction wherein a polyethylene glycol compound is contacted with an oxidant for a sufficient amount time to produce the dicarboxylic acid analogue of said polyethylene glycol compound. In some embodiments, the oxidation reaction is an oxoammonium-catalyzed oxidation reaction. In some embodiments, the oxidant is $NaClO_2$.

The synthesis method further comprises a subsequent step wherein the resulting dioic acid form of PEG is esterified to a lipid, the esterification reaction mediated by N-hydroxysuccinimide. In some embodiments, the resulting PEG-lipid is purified by chromatography.

The synthesis method further comprises a still further step wherein a bisphosphonate-PEG-lipid is synthesized by an esterification reaction. In some embodiments, the esterification reaction is mediated by N-hydroxysuccinimide. In some embodiments, the bisphosphonate-PEG-lipid is purified by chromatography.

In some embodiments, the bisphosphonate-PEG-lipid is a compound of Formula IV. In some embodiments, the bisphosphonate-PEG-lipid is a compound of Formula I. In some embodiments, the bisphosphonate-PEG-lipid is a compound of Formula Ia. In some embodiments, the bisphosphonate-PEG-lipid is the compound of Formula Ib.

Methods of Making PEG-Lipid Mixtures

In another aspect, the present disclosure provides a method of making a phospholipid composition capable of assembling containing a fluid having a normal boiling point of less than 30° C. The method comprises the steps of: (a) blending of PEG-lipids, including a bisphosphonate-PEG-lipid, (b) homogenization, and (c) filtration.

In typical embodiments, step (a) comprises blending a bisphosphonate-PEG-lipid, a compound of Formula II, and a compound of Formula III.

In typical embodiments, the bisphosphonate-PEG-lipid is a compound of Formula IV. In certain embodiments, the compound of Formula IV is a compound of Formula 1. In particular embodiments, the compound of Formula I is a compound of Formula Ia. In particular embodiments, the compound of Formula I is the compound of Formula Ib.

In some embodiments, the compound of Formula II is a compound of Formula IIa. In some embodiments, the compound of Formula II is the compound of Formula IIb. In some embodiments, compound of Formula III is a compound of Formula IIIa.

In step (b), the blended mixture of PEG-lipids is homogenized.

In step (c), the homogenized mixture is filtered.

Method of Manufacturing Microspheres

In a further aspect, the present disclosure provides for a method of manufacturing microspheres, the method comprising (a) preparing a PEG-lipid mixture as set forth in the section above, the mixture optionally further comprising at least one pharmaceutically acceptable excipient; and combining with water; (b) combining the PEG-lipid mixture of step (a) in a vessel with a fluid having a normal boiling point of less than 30° C.; and (c) agitating or otherwise energizing the vessel comprising the PEG-lipid mixture and fluid from step (b) to obtain microspheres. In some embodiments, microspheres obtained from step (c) are provided for therapeutic use. In this case, the microspheres can be in a liquid composition. The liquid composition can be in a container.

In some embodiments, the method further comprises step (d), processing the composition containing microspheres to lengthen its shelf life or expand the range of environmental conditions for storage. In one embodiment, step (d) involves lyophilizing the composition comprising microspheres, but other methods known in the art can be used to lengthen shelf life of microsphere solution or expand the range of environmental conditions for storage.

In some embodiments, the method further comprises filling the composition comprising the microspheres from step (c) or (d) into containers. In some embodiments, the method further comprises performing certain of the processing steps in containers. In some embodiments, the method further comprises the step of stoppering the containers comprising the microspheres from step (c) or (d).

In some embodiments, the method further comprises aseptic processing.

In some embodiments, the phospholipid composition of step (a) further comprises a compound of Formula II or a salt thereof. In some embodiments, the phospholipid composition of step (a) further comprises a compound of Formula III or a salt thereof. In some embodiments, the phospholipid composition of step (a) further comprises both a compound of Formula II or a salt thereof and a compound of Formula III or a salt thereof.

In some embodiments, the compound of Formula I or a salt thereof used in the method is a compound of Formula Ia, or a compound of Formula Ib. In some embodiments, the compound of Formula II or a salt thereof used in the method is a compound of Formula IIa or a compound of Formula IIb. In some embodiments, the compound of Formula III or a salt thereof used in the method is a compound of Formula IIIa.

In some embodiments, the phospholipid composition of step (a) is filtered prior to step (b).

In some embodiments, the phospholipid composition is transferred to a vessel after step (a) and before step (b). In some embodiments, some or all of steps (a)-(d) are performed by continuous processing.

In some embodiments, the lyophilized microspheres exist as lyophilized dry powder or as water-free concentrate.

In some embodiments, the vessel may be stoppered while under vacuum.

In some embodiments, the lyophilized microspheres are more stable than the microsphere solutions. In some embodiments, the lyophilized microspheres have longer shelf life than the microsphere solutions.

In some embodiments, the vessel is a unit dosage container.

In some embodiments, the fluid is n-decafluorobutane.

In some embodiments, the capped vessel is filled with n-decafluorobutane.

In some embodiments, the phospholipid composition of step (a) comprises liposomes with a mean diameter from 40 nanometers to 5000 nanometers. In some embodiments, the phospholipid composition of step (a) comprises liposomes with a mean diameter from 100 nanometers to 1000 nanometers, 200 nanometers to 900 nanometers, 300 nanometers to 800 nanometers, 400 nanometers to 700 nanometers, 500 nanometers to 600 nanometers, 100 nanometers to 200 nanometers, or 10 nanometers to 100 nanometers. In some embodiments, the mean diameter of the liposomes in the phospholipid composition of step (a) is about 50 nanometers.

In some embodiments, the method manufactures energy-responsive microspheres. For example, the microspheres generated by the method can collapse in response to application of energy. In some embodiments, the energy is in the form of electromagnetic, acoustic, microwave, photonic, or other forms. The collapse of the microspheres can release energy, e.g., mechanical energy.

In some embodiments, the mean diameter of the microspheres before lyophilization is about 0.1 microns to 1000 microns. In some embodiments, the mean diameter of the microspheres before lyophilization is about 0.1 microns to 100 microns. In some embodiments, the mean diameter of the microspheres before lyophilization is about 0.1 microns to 30 microns. In some embodiments, the mean diameter of the microspheres before lyophilization is about 0.7 microns to 10 microns. In some embodiments, the mean diameter of the microspheres before lyophilization is about 0.5 microns to 15.0 microns. In some embodiments, the mean diameter of the microspheres before lyophilization is about 1.0 microns to 10.0 microns. In some embodiments, the mean diameter of the microspheres before lyophilization is about 1.0 microns to 8.0 microns. In some embodiments, the mean diameter of the microspheres before lyophilization is about 1.0 microns to 7.0 microns. In some embodiments, the mean diameter of the microspheres before lyophilization is about 1.0 microns to 6.0 microns. In some embodiments, the mean diameter of the microspheres before lyophilization is about 1.0 microns to 5.0 microns. In some embodiments, the mean diameter of the microspheres before lyophilization is about 1.0 microns to 4.0. In some embodiments, the mean diameter of the microspheres before lyophilization is about 1.0 microns to 3.0 microns. In some embodiments, the mean diameter of the microspheres before lyophilization is about 1.0 microns to 2.0 microns.

In some embodiments, the method comprises step (d) involving lyophilizing the composition comprising microspheres, and loss of microspheres during lyophilization is no more than 50%. In some embodiments, the loss of the microspheres during lyophilization is no more than 40%. In some embodiments, the loss of the microspheres during lyophilization is no more than 30%. In another embodiment, the loss of the microspheres during lyophilization is no more than 25%. In some embodiments, the loss of the microspheres during lyophilization is no more than 20%. In some embodiments, the loss of the microspheres during lyophilization is no more than 15%. In some embodiments, the loss of the microspheres during lyophilization is no more than 10%.

In some embodiments, the molecular weight of the compound of Formula I is 1,500 to 5,000 Daltons. In some embodiments, the molecular weight of the compound of Formula I is 2,000 to 5,000 Daltons. In some embodiments, the molecular weight of the compound of Formula I is 2,000 to 4,500 Daltons. In some embodiments, the molecular weight of the compound of Formula I is 2,500 to 4,000 Daltons. In some embodiments, the molecular weight of the compound of Formula I is 3,000 to 3,500 Daltons.

In some embodiments, the molecular weight of the compound of Formula II is 1,500 to 5,000 Daltons. In some embodiments, the molecular weight of the compound of Formula II is 2,000 to 4,500 Daltons. In some embodiments, the molecular weight of the compound of Formula II is 2,500 to 4,000 Daltons. In some embodiments, the molecular weight of the compound of Formula II is 3,000 to 3,500 Daltons.

In some embodiments, the molecular weight of the compound of Formula III is 500 to 2,000 Daltons. In some embodiments, the molecular weight of the compound of Formula III is 750 to 1,750 Daltons. In some embodiments, the molecular weight of the compound of Formula III is 1,000 to 1,500 Daltons. In some embodiments, the molecular weight of the compound of Formula III is 1,100 to 1,400 Daltons. In some embodiments, the molecular weight of the compound of Formula III is 1200 to 1,300 Daltons.

In some embodiments, the microspheres obtained from step (c) comprise 0.01-5 mol % of a compound of Formula I. In some embodiments, the microspheres comprise 0.05-5 mol % of a compound of Formula I. In some embodiments, the microspheres comprise 0.1-5 mol % of a compound of Formula I. In some embodiments, the microspheres comprise 0.5-4.5 mol % of a compound of Formula I. In some embodiments, the microspheres comprise 1.0-4.0 mol % of a compound of Formula I. In some embodiments, the microspheres comprise 1.5-3.5 mol % of a compound of Formula I. In some embodiments, the microspheres comprise 2.0-3.0 mol % of a compound of Formula I.

In some embodiments, the microspheres obtained from step (c) comprise 5-9.9 mol % of a compound of Formula II. In some embodiments, the microspheres comprise 5.5-9.5 mol % of a compound of Formula II. In some embodiments, the microspheres comprise 6.0-9.0 mol % of a compound of Formula II. In some embodiments, the microspheres comprise 6.5-8.5 mol % of a compound of Formula II. In some embodiments, the microspheres comprise 7.0-8.0 mol % of a compound of Formula II.

In some embodiments, the microspheres obtained from step (c) comprise 80-95 mol % of the compound of Formula III. In some embodiments, the microspheres comprise 82.5-92.5 mol % of the compound of Formula III. In some embodiments, the microspheres comprise 85-90 mol % of the compound of Formula III. In some embodiments, the microspheres comprise 87.5-92.5 mol % of the compound of Formula III.

In some embodiments, the microspheres obtained from step (c) comprise no more than 5 mol % of the compound of Formula I. In some embodiments, the microspheres obtained from step (c) comprise no more than 4.5 mol % of a compound of Formula I. In some embodiments, the microspheres comprise no more than 4.0 mol % of a compound of Formula I. In some embodiments, the microspheres comprise no more than 3.5 mol % of a compound of Formula I. In some embodiments, the microspheres comprise no more than 3.0 mol % of a compound of Formula I. In some embodiments, the microspheres comprise no more than 2.5 mol % of a compound of Formula I. In some embodiments, the microspheres comprise no more than 2.0 mol % of a compound of Formula I. In some embodiments, the microspheres comprise no more than 1.5 mol % of a compound of Formula I. In some embodiments, the microspheres comprise no more than 1.0 mol % of a compound of Formula I. In some embodiments, the microspheres comprise no more than 0.5 mol % of a compound of Formula I. In some embodiments, the microspheres comprise no more than 0.1 mol % of a compound of Formula I. In some embodiments, the microspheres comprise no more than 0.05 mol % of a compound of Formula I.

In some embodiments, the microspheres obtained from step (c) comprise no more than 10 mol % of the compound of Formula II. In some embodiments, the microspheres comprise no more than 9.5 mol % of a compound of Formula II. In some embodiments, the microspheres comprise no more than 9.0 mol % of a compound of Formula II. In some embodiments, the microspheres comprise no more than 8.5 mol % of a compound of Formula II. In another embodiment, the microspheres comprise no more than 8.0 mol % of a compound of Formula II. In another embodiment, the microspheres comprise no more than 7.5 mol % of a compound of Formula II. In some embodiments, the microspheres comprise no more than 7.0 mol % of a compound of Formula II. In some embodiments, the microspheres comprise no more than 6.5 mol % of a compound of Formula II. In some embodiments, the microspheres comprise no more than 6.0 mol % of a compound of Formula II. In some embodiments, the microspheres comprise no more than 5.5 mol % of a compound of Formula II. In some embodiments, the microspheres comprise no more than 5.0 mol % of a compound of Formula II.

In some embodiments, the microspheres obtained from step (c) comprise no more than 95 mol % of the compound of Formula III. In some embodiments, the microspheres comprise no more than 92.5 mol % of the compound of Formula III. In some embodiments, the microspheres comprise no more than 90 mol % of the compound of Formula III. In some embodiments, the microspheres comprise no more than 87.5 mol % of the compound of Formula III. In some embodiments, the microspheres comprise no more than 85.0 mol % of the compound of Formula III. In some embodiments, the microspheres comprise no more than 82.5 mol % of the compound of Formula III. In some embodiments, the microspheres comprise no more than 80.0 mol % of the compound of Formula III.

In some embodiments, the average molecular weight of the compound of Formula Ib in the microspheres of step (c) is about 3500 Daltons. In some embodiments, the average molecular weight of the compound of Formula Ib is about 3200 Daltons. In some embodiments, the average molecular weight of the compound of Formula Ib is about 2500 Daltons. In some embodiments, the average molecular weight of the compound of Formula Ib is about 2000 Daltons.

In some embodiments, the average molecular weight of the compound of Formula IIb in the microspheres of step (c) is about 3000 Daltons. In some embodiments, the average molecular weight of the compound of Formula IIb is about 2800 Daltons. In some embodiments, the average molecular weight of the compound of Formula IIb is about 2600 Daltons. In some embodiments, the average molecular weight of the compound of Formula IIb is about 2400 Daltons. In some embodiments, the average molecular weight of the compound of Formula IIb is about 2200 Daltons. In some embodiments, the average molecular weight of the compound of Formula IIb is about 2000 Daltons.

In some embodiments, the average molecular weight of the compound of Formula IIIa in the microspheres of step (c) is about 840 Daltons. In some embodiments, the average molecular weight of the compound of Formula IIIa is about 790 Daltons. In some embodiments, the average molecular weight of the compound of Formula IIIa is about 750 Daltons. In some embodiments, the average molecular weight of the compound of Formula IIIa is about 700 Daltons. In some embodiments, the average molecular weight of the compound of Formula IIIa is about 650 Daltons.

In some embodiments, the microspheres obtained from step (c) comprise 0.01-5 mol % of the compound of Formula Ib. In some embodiments, the microspheres comprise 0.05-5 mol % of the compound of Formula Ib. In some embodiments, the microspheres comprise 0.1-5 mol % of the compound of Formula Ib. In some embodiments, the microspheres comprise 0.5-4.5 mol % of a compound of Formula Ib. In some embodiments, the microspheres comprise 1.0-4.0 mol % of a compound of Formula Ib. In some embodiments, the microspheres comprise 1.5-3.5 mol % of a compound of Formula Ib. In some embodiments, the microspheres comprise 2.0-3.0 mol % of a compound of Formula Ib.

In some embodiments, the microspheres obtained from step (c) comprise 5-9.9 mol % of the compound of Formula IIb. In some embodiments, the microspheres comprise 6.0-9.0 mol % of a compound of Formula IIb. In some embodiments, the microspheres comprise 6.5-8.5 mol % of a compound of Formula IIb. In some embodiments, the microspheres comprise 7.0-8.0 mol % of a compound of Formula IIb.

In some embodiments, the microspheres obtained from step (c) comprise 80-95 mol % of the compound of Formula IIIa. In some embodiments, the microspheres comprise 82.5-92.5 mol % of the compound of Formula IIIa. In some embodiments, the microspheres comprise 85-90 mol % of the compound of Formula IIIa. In some embodiments, the microspheres comprise 87.5-92.5 mol % of the compound of Formula IIIa.

In some embodiments, the microspheres obtained from step (c) comprise no more than 5 mol % of the compound of Formula Ib. In some embodiments, the microspheres comprise no more than 4.5 mol % of a compound of Formula Ib. In some embodiments, the microspheres comprise no more than 4.0 mol % of a compound of Formula Ib. In some embodiments, the microspheres comprise no more than 3.5 mol % of a compound of Formula Ib. In some embodiments, the microspheres comprise no more than 3.0 mol % of a compound of Formula Ib. In some embodiments, the microspheres comprise no more than 2.5 mol % of a compound of Formula Ib. In some embodiments, the microspheres comprise no more than 2.0 mol % of a compound of Formula Ib. In some embodiments, the microspheres comprise no more than 1.5 mol % of a compound of Formula Ib. In some embodiments, the microspheres comprise no more than 1.0 mol % of a compound of Formula Ib. In some embodiments, the microspheres comprise no more than 0.5 mol % of a compound of Formula Ib. In some embodiments, the microspheres comprise no more than 0.1 mol % of a compound of Formula Ib. In some embodiments, the microspheres comprise no more than 0.05 mol % of a compound of Formula Ib.

In some embodiments, the microspheres obtained from step (c) comprise no more than 10 mol % of the compound of Formula IIb. In some embodiments, the microspheres comprise no more than 9.5 mol % of a compound of Formula IIb. In some embodiments, the microspheres comprise no more than 9.0 mol % of a compound of Formula IIb. In some embodiments, the microspheres comprise no more than 8.5 mol % of a compound of Formula IIb. In some embodiments, the microspheres comprise no more than 8.0 mol % of a compound of Formula IIb. In some embodiments, the microspheres comprise no more than 7.5 mol % of a compound of Formula IIb. In some embodiments, the microspheres comprise no more than 7.0 mol % of a compound of Formula IIb. In some embodiments, the microspheres comprise no more than 6.5 mol % of a compound of Formula IIb. In some embodiments, the microspheres comprise no more than 6.0 mol % of a compound of Formula IIb. In some embodiments, the microspheres comprise no more than 5.5 mol % of a compound of Formula IIb. In some embodiments, the microspheres comprise no more than 5.0 mol % of a compound of Formula IIb.

In some embodiments, the microspheres obtained from step (c) comprise no more than 95 mol % of the compound of Formula IIIa. In some embodiments, the microspheres comprise no more than 92.5 mol % of the compound of Formula IIIa. In some embodiments, the microspheres comprise no more than 90 mol % of the compound of Formula IIIa. In some embodiments, the microspheres comprise no more than 87.5 mol % of the compound of Formula IIIa. In some embodiments, the microspheres comprise no more than 85.0 mol % of the compound of Formula IIIa. In some embodiments, the microspheres comprise no more than 82.5 mol % of the compound of Formula IIIa. In some embodiments, the microspheres comprise no more than 80.0 mol % of the compound of Formula IIIa.

In some embodiments, the molar ratio of the compound of Formula Ia to the compound of Formula IIa in the microspheres obtained from step (c) ranges from 1:1000 to 1:1. In some embodiments of the microspheres, the molar ratio of the compound of Formula Ia to the compound of Formula IIa ranges from 1:500 to 1:1. In some embodiments of the microspheres, the molar ratio of the compound of Formula Ia to the compound of Formula IIa ranges from 1:100 to 1:1. In some embodiments, the molar ratio of the compound of Formula Ia to the compound of Formula IIa ranges from 1:90 to 1:5. In some embodiments, the molar ratio of the compound of Formula Ia to the compound of Formula IIa ranges from 1:80 to 1:10. In some embodiments, the molar ratio of the compound of Formula Ia to the compound of Formula IIa ranges from 1:70 to 1:20. In some embodiments, the molar ratio of the compound of Formula Ia to the compound of Formula IIa ranges from 1:60 to 1:30. In some embodiments, the molar ratio of the compound of Formula Ia to the compound of Formula IIa ranges from 1:50 to 1:40.

In some embodiments of the pharmaceutical composition, the molar ratio of the compound of Formula IIa to the compound of Formula IIIa ranges from 1:20 to 1:8. In some embodiments, the molar ratio of the compound of Formula IIa to the compound of Formula IIIa ranges from 1:18 to 1:10. In some embodiments, the molar ratio of the compound of Formula IIa to the compound of Formula IIIa ranges from 1:16 to 1:12. In some embodiments, the molar ratio of the compound of Formula IIa to the compound of Formula IIIa ranges from 1:15 to 1:13.

In some embodiments of the microspheres, the molar ratio of the compound of Formula Ib to the compound of Formula IIb ranges from 1:1000 to 1:1. In some embodiments of the microspheres, the molar ratio of the compound of Formula Ib to the compound of Formula IIb ranges from 1:500 to 1:1. In some embodiments of the microspheres, the molar ratio of the compound of Formula Ib to the compound of Formula IIb ranges from 1:100 to 1:1. In some embodiments, the molar ratio of the compound of Formula Ib to the compound of Formula IIb ranges from 1:90 to 1:5. In some embodiments, the molar ratio of the compound of Formula Ib to the compound of Formula IIb ranges from 1:80 to 1:10. In some embodiments, the molar ratio of the compound of Formula Ib to the compound of Formula IIb ranges from 1:70 to 1:20. In some embodiments, the molar ratio of the compound of Formula Ib to the compound of Formula IIb ranges from 1:60 to 1:30. In some embodiments, the molar ratio of the compound of Formula Ib to the compound of Formula IIb ranges from 1:50 to 1:40.

Unit Dosage Form

In a fourth aspect, the present disclosure provides for a unit dosage container comprising a therapeutically effective amount of the pharmaceutical composition described herein.

In some embodiments, the unit dosage container comprises a phosphilipid composition, wherein the phospholipid composition comprises a compound of Formula I, a compound of Formula II, and a compound of Formula III, and at least one pharmaceutically acceptable excipients. In some embodiments, the unit dosage container further comprises a fluid with a normal boiling point less than 30° C.

In some embodiments, the unit dosage container comprises microspheres, wherein the microspheres comprise a compound of Formula I, a compound of Formula II, a compound of Formula III, a fluid with a normal boiling point less than 30° C., and at least one pharmaceutically acceptable excipients. The microspheres can be obtained by the method described herein related to the method of manufacturing microspheres.

In some embodiments of the unit dosage form, the compound of Formula I is a compound of Formula Ia or Ib.

In some embodiments of the unit dosage form, the compound of Formula II is a compound of Formula IIa or IIb.

In some embodiments of the unit dosage form, the compound of Formula III is a compound of Formula IIIa.

In some embodiments, the fluid with a normal boiling point of less than 30° C. is a gas at body temperature. In some embodiments, the fluid is air, $CO_2$, sulfur hexafluoride, a fluorinated $C_{1-6}$ alkane, or a combination thereof.

In some embodiments, the fluid is n-decafluorobutane.

In some embodiments, the composition of the unit dosage container further comprises trehalose and PLASDONE K12 as excipients. In some embodiments, the unit dosage container further comprises phosphate buffered solution without calcium and magnesium ions.

In some embodiments, the composition of the unit dosage container is capable of forming microspheres in the presence of water. In some embodiments, the composition of the unit dosage container is a liquid composition comprising microspheres.

In some embodiments, the microspheres of the unit dosage container exist as lyophilized dry powder or as water-free concentrate. In some embodiments, the lyophilized dry powder is the lyophalate comprising of microspheres. In some embodiments, the composition of the unit dosage container is a product obtained by reconstitution of a lyophilized formulation comprising microspheres.

In some embodiments, the residual water content of the lyophalate comprising the microspheres is no more than 10% by weight. In some embodiments, the residual water content of the lyophalate comprising the microspheres is no more than 9.5% by weight. In some embodiments, the residual water content of the lyophalate comprising the microspheres is no more than 9.0% by weight. In some embodiments, the residual water content of the lyophalate comprising the microspheres is no more than 8.5% by weight. In some embodiments, the residual water content of the lyophalate comprising the microspheres is no more than 8.0% by weight. In some embodiments, the residual water content of the lyophalate comprising the microspheres is no more than 7.5% by weight. In some embodiments, the residual water content of the lyophalate comprising the microspheres is no more than 7.0% by weight. In some embodiments, the residual water content of the lyophalate comprising the microspheres is no more than 6.5% by weight. In some embodiments, the residual water content of the lyophalate comprising the microspheres is no more than 6.0% by weight. In some embodiments, the residual water content of the lyophalate comprising the microspheres is no more than 5.5% by weight. In some embodiments, the residual water content of the lyophalate comprising the microspheres is no more than 5.0% by weight. In some embodiments, the residual water content of the lyophalate comprising the microspheres is no more than 4.5% by weight. In some embodiments, the residual water content of the lyophalate comprising the microspheres is no more than 4.0% by weight. In some embodiments, the residual water content of the lyophalate comprising the microspheres is no more than 3.5% by weight. In some embodiments, the residual water content of the lyophalate comprising the microspheres is no more than 3.0% by weight. In some embodiments, the residual water content of the lyophalate comprising the microspheres is no more than 2.5% by weight. In some embodiments, the residual water content of the lyophalate comprising the microspheres is no more than 2.0% by weight. In some embodiments, the residual water content of the lyophalate comprising the microspheres is no more than 1.5% by weight. In some embodiments, the residual water content of the lyophalate comprising the microspheres is no more than 1.0% by weight. In some embodiments, the residual water content of the lyophalate comprising the microspheres is no more than 0.5% by weight. In some embodiments, the residual water content of the lyophalate comprising the microspheres is no more than 0.4% by weight. In some embodiments, the residual water content of the lyophalate comprising the microspheres is no more than 0.3% by weight. In some embodiments, the residual water content of the lyophalate comprising the microspheres is no more than 0.2% by weight. In some embodiments, the residual water content of the lyophalate comprising the microspheres is no more than 0.1% by weight. In some embodiments, the residual water content of the lyophalate comprising the microspheres is no more than 0.01% by weight.

In some embodiments, the composition of the unit dosage container is prepared by any one of the methods described herein.

In some embodiments, the unit dosage container is sealed by a crimp-top cap fitted with a septum. In some embodiments, the unit dosage container is airtight.

Kits

In another aspect, the present disclosure provides for a kit comprising at least one unit dosage container as described herein and instructions for using said kit.

In some embodiments, the composition within each of the at least one unit dosage container is capable of forming microspheres in the presence of water.

In some embodiments of the kit, the unit dosage container further comprises trehalose and PLASDONE K12 as pharmaceutically acceptable excipients.

In some embodiments, the kit further comprises a container comprising an aqueous solution. In some embodiments, the aqueous solution is sterile water. In some embodiments, the aqueous solution is a saline solution ready for perfusion.

In some embodiments, the kit further comprises a syringe. In some embodiments, the kit further comprises a needle. In some embodiments, the kit further comprises a needle-free syringe (e.g., Mini-Spike®) comprising a sharp tip, wherein the needle-free syringe is capable of piercing through a stopper.

In some embodiments, the kit further comprises a container of fluid, wherein the fluid is air, nitrogen, argon, $CO_2$, sulfur hexafluoride, a fluorinated $C_{1-6}$ alkane, or a combination thereof. In some embodiments, the container is a syringe.

In some embodiments of the kit, the fluorinated $C_{1-6}$ alkane is selected from octafluoropropane, n-decafluorobutane, and dodecafluoropentane.

In some embodiments of the kit, the fluid is n-decafluorobutane.

In some embodiments, the kit further comprises a gel pad or ultrasound gel.

In some embodiments, the kit further comprises an apparatus selected from Mix2Vial® apparatus and a vented vial adapter.

Method of Reconstitution

In yet another aspect, the present disclosure provides for a method of reconstituting the microspheres as prepared according to any one of the methods as described herein. In some embodiments, lyophalate comprising of microspheres are reconstituted. In some embodiments, the method of reconstitution comprises adding a sufficient amount of sterile water or a saline solution to the microsphere solution described in the above sections in a container. The method can further comprise adding a volume of gas to the container and shaking the container. Specifically, in some embodiments, the method of reconstituting microspheres comprises:

(a) adding a sufficient amount of sterile water or a saline solution to the microspheres inside the container;
(b) optionally adding a volume of gas to the container of step (a); and
(c) optionally shaking the container of step (b).

In some embodiments of the method of reconstitution, the amount of sterile water or the saline solution is no more than 1000 milliliters. In some embodiments of the method of reconstitution, the amount of sterile water or the saline solution is no more than 750 milliliters. In some embodiments of the method of reconstitution, the amount of sterile water or the saline solution is no more than 500 milliliters. In some embodiments of the method of reconstitution, the amount of sterile water or the saline solution is no more than 200 milliliters. In some embodiments of the method of reconstitution, the amount of sterile water or the saline solution is no more than 100 milliliters. In some embodiments, the amount of sterile water or the saline solution is no more than 90 milliliters. In some embodiments, the amount of sterile water or the saline solution is no more than 80 milliliters. In some embodiments, the amount of sterile water or the saline solution is no more than 70 milliliters. In some embodiments, the amount of sterile water or the saline solution is no more than 60 milliliters. In some embodiments, the amount of sterile water or the saline solution is no more than 50 milliliters. In some embodiments, the amount of sterile water or the saline solution is no more than 40 milliliters. In some embodiments, the amount of sterile water or the saline solution is no more than 30 milliliters. In some embodiments, the amount of sterile water or the saline solution is no more than 20 milliliters. In some embodiments, the amount of sterile water or the saline solution is no more than 10 milliliters. In some embodiments, the amount of sterile water or the saline solution is no more than 5 milliliters. In some embodiments, the amount of sterile water or the saline solution is no more than 1 milliliters. In some embodiments, the amount of sterile water or the saline solution is no more than 0.5 milliliters. In some embodiments, the amount of sterile water or the saline solution is no more than 0.3 milliliters.

In some embodiments, the amount of the sterile water or the saline solution added is sufficient to produce a homogeneous mixture comprising the reconstituted microspheres.

In some embodiments of the method of reconstitution, the shaking of the container lasts no more than 180 seconds. In some embodiments, the shaking of the container lasts no more than 160 seconds. In some embodiments, the shaking of the container lasts no more than 140 seconds. In some embodiments, the shaking of the container lasts no more than 120 seconds. In some embodiments, the shaking of the container lasts no more than 100 seconds. In some embodiments, the shaking of the container lasts no more than 80 seconds. In some embodiments, the shaking of the container lasts no more than 60 seconds. In some embodiments, the shaking of the container lasts no more than 40 seconds. In some embodiments, the shaking of the container lasts no more than 20 seconds. In some embodiments, the shaking of the container lasts no more than 10 seconds. In some embodiments, the shaking of the container lasts no more than 5 seconds.

In some embodiments of the method of reconstitution, the shaking of the container lasts no more than 160 seconds. In some embodiments, the shaking of the container lasts at least 140 seconds. In some embodiments, the shaking of the container lasts at least 120 seconds. In some embodiments, the shaking of the container lasts at least 100 seconds. In some embodiments, the shaking of the container lasts at least 80 seconds. In some embodiments, the shaking of the container lasts at least 60 seconds. In some embodiments, the shaking of the container lasts at least 40 seconds. In some embodiments, the shaking of the container lasts at least 20 seconds. In some embodiments, the shaking of the container lasts at least 10 seconds. In some embodiments, the shaking of the container lasts at least 5 seconds.

Method of Treatment

In a final aspect, the present disclosure provides for a method of treating a medical condition involving an abnormal or obstructive mass. In some embodiments, the medical condition involves kidney stones, urinary stones, biliary stones, blood clots, fibroids, cancerous tumors, and atheromatous plaques. In some embodiments, the subject has urolithiasis.

In some embodiments, the method comprises: administering to a subject with the medical condition an effective amount of the reconstituted microsphere solution as described herein so as to bring the microspheres into contact with the abnormal or obstructive mass (e.g., urinary stone, kidney stone, biliary stones, blood clots, fibroids, cancerous tumors, and atheromatous plaques); and directionally applying an energy, at a frequency that excites the fluid within the microspheres, to the abnormal or obstructive mass within the subject.

In some embodiments, the reconstituted microsphere solution is administered into the ureter of the subject through a urinary catheter.

In some embodiments, the applied energy is in the form of electromagnetic, acoustic, microwave, photonic, laser, or other forms.

In some embodiments, the applied energy is ultrasonic. In some embodiments, the applied energy is acoustic energy.

In some embodiments, the acoustic energy is ultrasonic energy in the frequency range from 100 kilohertz (kHz) to 2 megahertz (MHz). In some embodiments, the acoustic energy is ultrasonic energy in the frequency range from 200 kilohertz (kHz) to 1.5 megahertz (MHz). In some embodiments, the acoustic energy is ultrasonic energy in the frequency range from 300 kilohertz (kHz) to 1.2 megahertz (MHz). In some embodiments, the acoustic energy is ultrasonic energy in the frequency range from 500 kilohertz (kHz) to 1 megahertz (MHz).

In some embodiments, the applied ultrasonic energy is associated with peak pressures in the range 0.1 MPa to 10 MPa. In some embodiments, the applied ultrasonic energy is associated with peak pressures in the range 1 MPa to 10 MPa. In some embodiments, the applied ultrasonic energy is associated with peak pressures in the range 2 MPa to 9 MPa. In some embodiments, the applied ultrasonic energy is associated with peak pressures in the range 4 MPa to 8 MPa. In some embodiments, the applied ultrasonic energy is associated with peak pressures in the range 5 MPa to 7 MPa.

In some embodiments, the applied energy is generated with intraluminal energy from solid-state, pulsed laser.

In some embodiments, the wavelength of the laser energy is in the range 1000 nm to 2500 nm. In some embodiments, the wavelength of the laser energy is in the range 2050 nm to 2150 nm. In some embodiments, the vaporization of a liquid phase by the laser energy is associated with a moving phase boundary that produces pressure effects in the liquid phase.

In some embodiments, the laser energy has a frequency in the range between 1 kHz to 1 MHz. In some embodiments, the laser energy has a frequency in the range between 1 kHz to 1 MHz, between 10 kHz to 500 kHz, between 50 kHz to 100 kHz, or between 10 kHz to 50 kHz.

In some embodiments, the energy is applied for a sufficient amount of time to fragment the urinary stone.

In some embodiments, the amount of time of the applied energy is no more than 100 minutes. In some embodiments, the amount of time of the applied energy is no more than 90 minutes. In some embodiments, the amount of time of the applied energy is no more than 80 minutes. In some embodiments, the amount of time of the applied energy is no more than 70 minutes. In some embodiments, the amount of time of the applied energy is no more than 60 minutes. In some embodiments, the amount of time of the applied energy is no more than 50 minutes. In some embodiments, the amount of time of the applied energy is no more than 40 minutes. In some embodiments, the amount of time of the applied energy is no more than 30 minutes. In some embodiments, the amount of time of the applied energy is no more than 25 minutes. In some embodiments, the amount of time of the applied energy is no more than 20 minutes. In some embodiments, the amount of time of the applied energy is no more than 15 minutes. In some embodiments, the amount of time of the applied energy is no more than 10 minutes.

In some embodiments, the applied photonic energy causes a change in volume of the microspheres or other cavitation effects of the microspheres.

In some embodiments, the cavitation of the microspheres causes pressure gradient changes and mechanical effects in the urinary stone around the reconstituted microspheres.

In some embodiments, the pressure gradient changes and other mechanical effects are capable of fragmenting urinary stones.

In some embodiments, the subject is human. In some embodiments, the subject is an animal.

EXAMPLES

The following synthetic and biological examples are offered to illustrate the present technology and are not to be construed in any way as limiting the scope of the present technology.

Unless otherwise stated, all temperatures are in degrees Celsius.

Efforts have been made to ensure accuracy with respect to numbers used (e.g., amounts, temperatures, etc.), but some experimental error and deviation should be allowed for.

Any methods that are functionally equivalent are within the scope of the present technology. Various modifications of the present technology in addition to those described herein will become apparent to those skilled in the art from the foregoing description and accompanying figures. Such modifications fall within the scope of the appended claims.

In the examples below, the following abbreviations have the following meanings. If an abbreviation is not defined, it has its generally accepted meaning.

aq.=aqueous
LC-MS=liquid chromatography-mass spectrometry
MS=mass spectrometry
THF=tetrahydrofuran
$NaHCO_3$=sodium bicarbonate
DIEA=diisopropylethylamine
MS=mass spectrometry
NaH=sodium hydride
o/n=overnight
HATU=1-[Bis(dimethylamino)methylene]-1H-1,2,3-trI zolo[4,5-b]pyridinium 3-oxid hexafluorophosphate
r.t.=room temperature
LAH=lithium aluminum hydride
DCM=dichloromethane
DMF=dimethylformamide
DMSO=dimethyl sulfoxide
equiv.=equivalent
EtOAc=ethyl acetate
EtOH=ethanol
g=gram
h=hours
HCl=hydrochloric acid
HPLC=high-performance liquid chromatography
HOAc=acetic acid
M=molar
MeOH=methanol
mg=milligrams
mL=milliliters
mmol=millimols
mp=melting point
m/z=mass to charge ratio
NaCl=sodium chloride
$Na_2CO_3$=sodium carbonate
NMR=nuclear magnetic resonance
NaOH=sodium hydroxide
$Na_2SO_4$=sodium sulfate
NHS=n-hydroxysuccinimide
ppm=parts per million
TLC=thin layer chromatography
UV=ultraviolet
wt %=weight percent
µM=micromolar General Experimental Details:

Final compounds and phospholipid composition were confirmed by NMR. $^1$H-NMR, $^{31}$P-NMR, $^{13}$C-NMR spectra were recorded in $CDCl_3$ (residual internal standard $CHCl_3$=δ 7.26), DMSO-$d_6$ (residual internal standard $CD_3SOCD_2H$=δ 2.50), methanol-$d_4$ (residual internal standard $CD_2HOD$=δ 3.20), or acetone-$d_6$ (residual internal standard $CD_3COCD_2H$=δ 2.05), or a mixture of $CDCl_3$ and methanol-$d_4$. The chemical shifts (δ) reported are given in parts per million (ppm) and the coupling constants (J) are in Hertz (Hz). The spin multiplicities are reported as s=singlet, bs=broad singlet, bm=broad multiplet, d=doublet, t=triplet, q=quartet, p=pentuplet, dd=doublet of doublet, ddd=doublet of doublet of doublet, dt=doublet of triplet, td=triplet of doublet, tt=triplet of triplet, and m=multiplet.

Example 1: Synthesis of the Compound of Formula Ib

Step 1—Synthesis of PEG2DA

Figure 8:
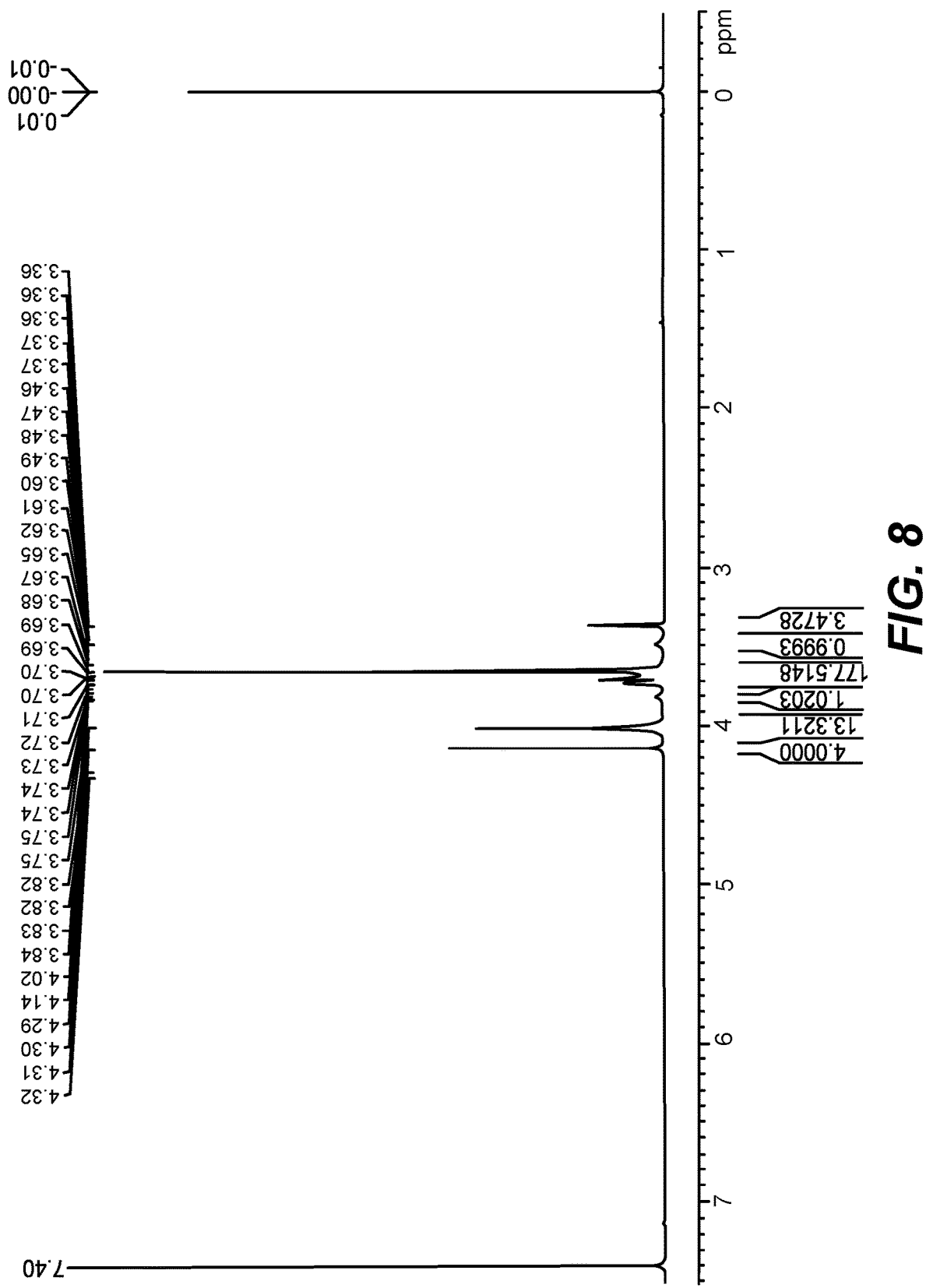
FIG. 8 shows the $^1$H-NMR spectrum of intermediate PEG2DA.

PEG2000 was dissolved in acetonitrile and warmed to 40° C. Following dissolution, an aqueous potassium phosphate buffer adjusted to pH ~7.5 with phosphoric acid is charged, followed by the addition of TEMPO. Aqueous solutions of sodium chlorite and sodium hypochlorite are then simultaneously charged to the reaction mixture over the course of 30 minutes to 1 hour. When the charge is complete, the reaction is stirred at 40° C. for a minimum of 24-48 hours. After the minimum stir time, the reaction is assayed for completion by TLC analysis. When deemed complete, the mixture is cooled to 0° C. and quenched with an aqueous sodium thiosulfate solution. The quenched solution is then acidified with aqueous hydrochloric acid to pH<3 and the organic material is extracted with chloroform/methanol/water partitions. Solvent is then removed from the organic phase via rotary evaporation and the material is dried with toluene cycles. The crude material is then purified by precipitation from toluene with diethyl ether. FIG. 8 shows the $^1$H-NMR spectrum of purified PEG2DA.

Step 2—Synthesis of DSPE-PEG2-COOH

Figure 9:
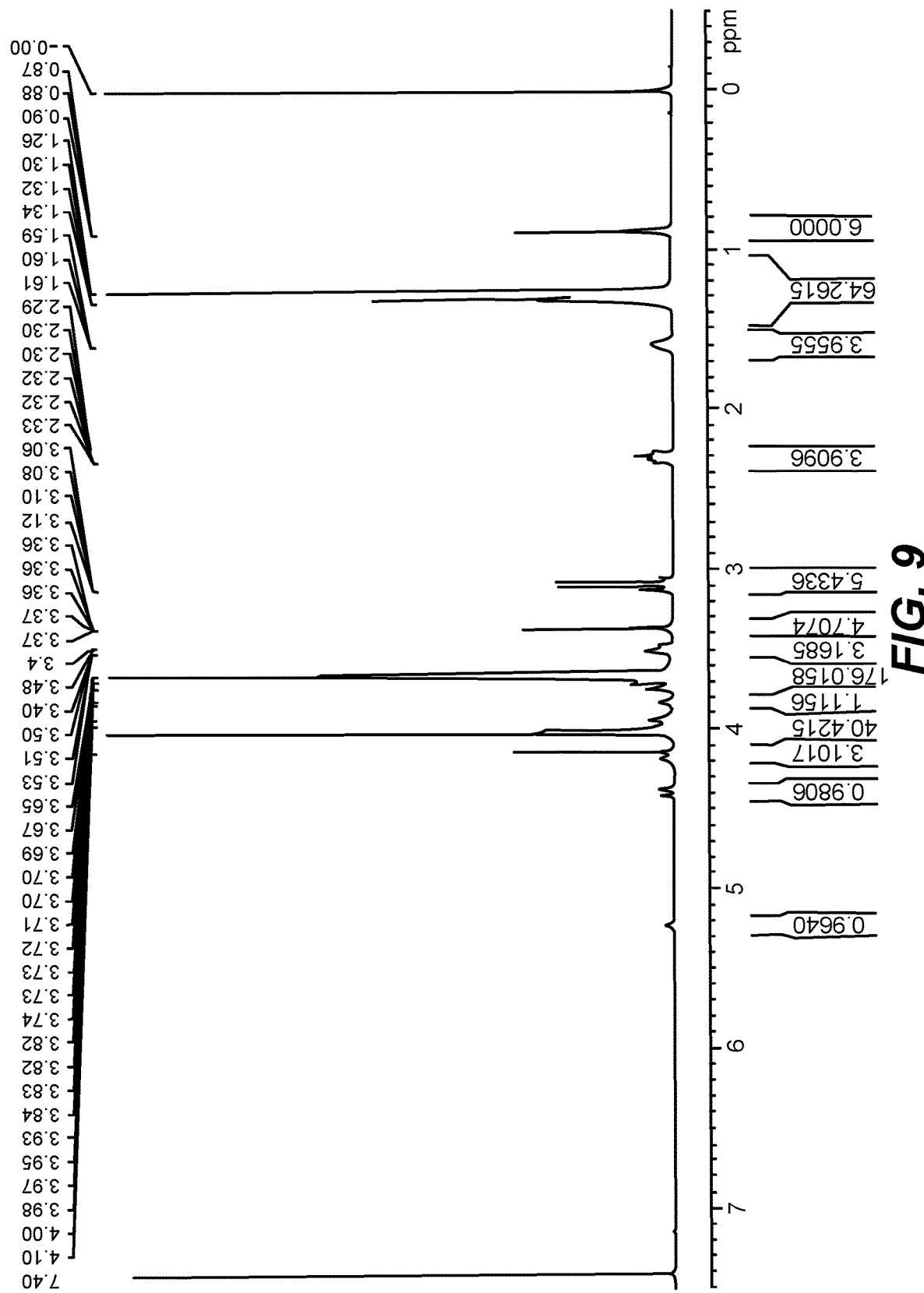
FIG. 9 shows the $^1$H-NMR spectrum of intermediate 1,2-distearoyl-sn-glycero-3-phosphoethanolamine-N-[methoxy(polyethylene glycol)-2000] (DSPE-PEG2)-COOH.
Figure 10:
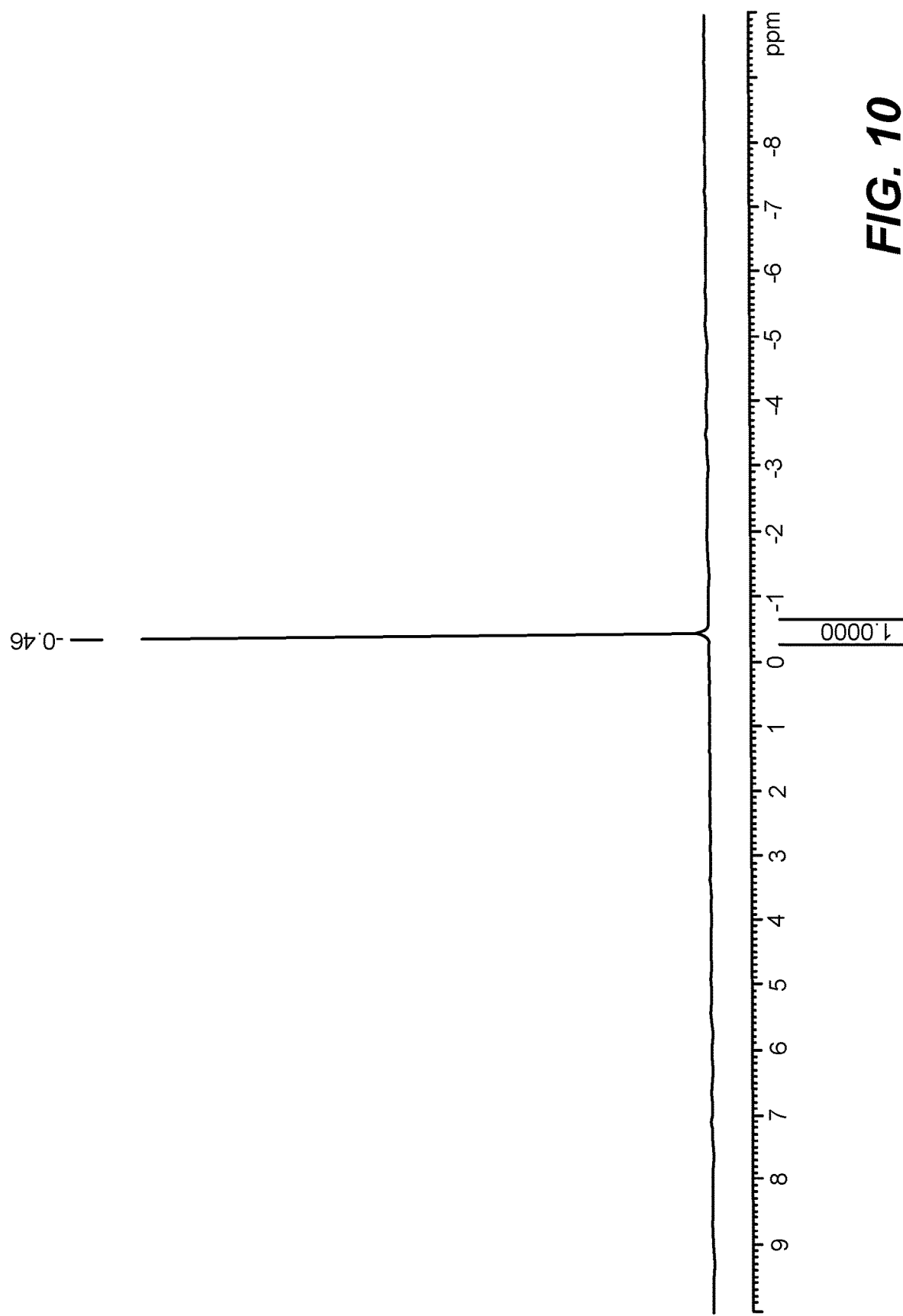
FIG. 10 shows the $^{31}$P-NMR spectrum of intermediate 1,2-distearoyl-sn-glycero-3-phosphoethanolamine-N-[methoxy(polyethylene glycol)-2000] (DSPE-PEG2)-COOH.

PEG2DA was dissolved in toluene and warmed to 90° C. CDI was added portion-wise to control carbon dioxide evolution. Once all solids were dissolved and all bubbling has ceased, solid DSPE was added to the reaction mixture, followed by triethylamine. The mixture was stirred at 90° C. for 12-24 hours, at which time reaction completion was checked by TLC. Once complete, the reaction mixture was quenched with 5-10 mL of methanol and cooled to ambient temperature. Once cooled, the solution was diluted with chloroform and partitioned against 1 M aqueous hydrochloric acid to remove imidazole, followed by a brine wash. The mixture was neutralized with ammonium hydroxide prior to bulk solvent removal via rotary evaporation. The crude mixture was then sequentially chromatographed first with normal phase media (chloroform/methanol/ammonium hydroxide gradient) then with reverse phase media (methanol/water gradient) including a column wash with sodium chloride to achieve the sodium salt of DSPE-PEG2—COOH. FIGS. 9 and 10 show the $^1$H-NMR and $^{31}$P-NMR spectra of DSPE-PEG2-COOH respectively.

Step 3—Synthesis of the Compound of Formula Ib

Figure 11:
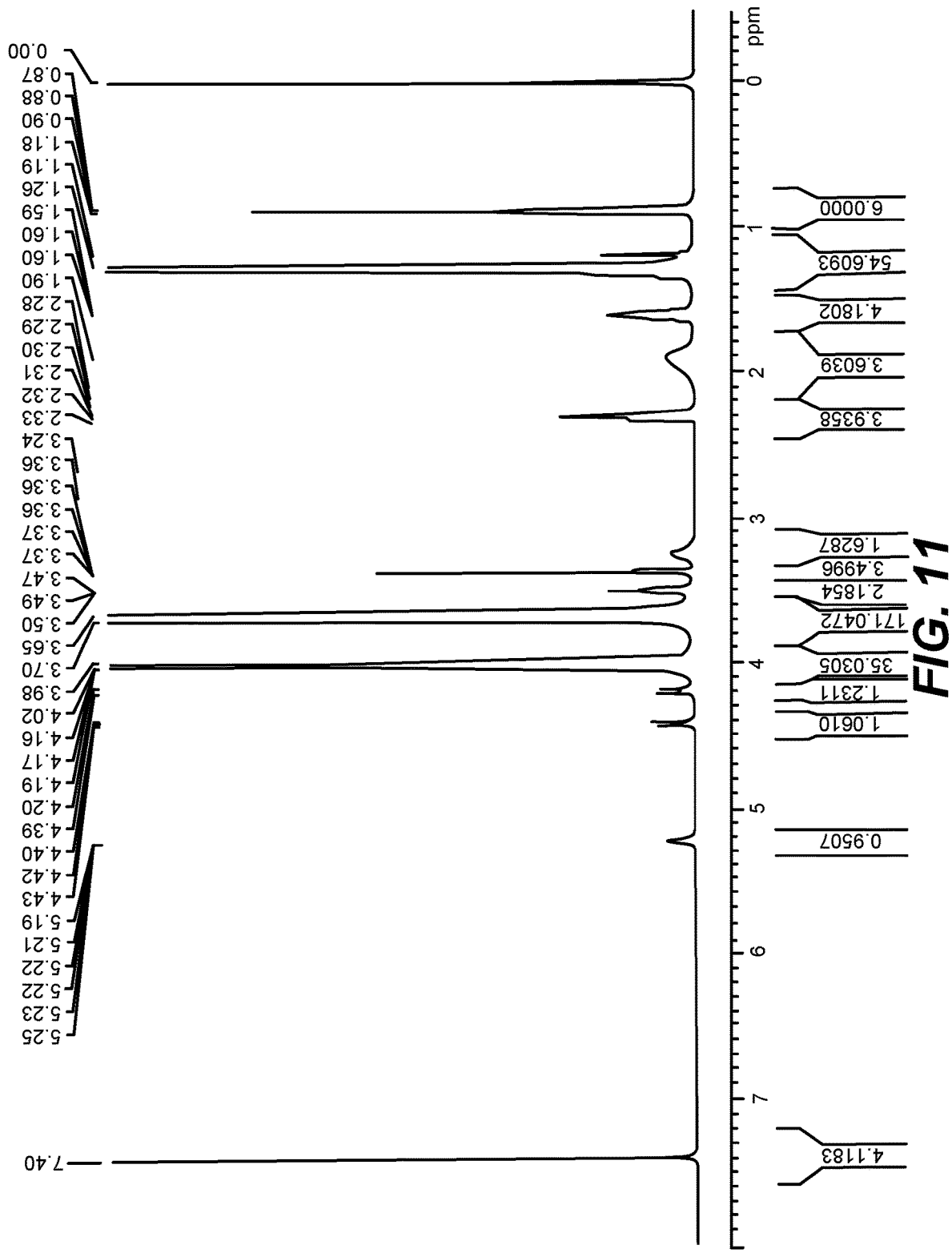
FIG. 11 shows the $^1$H-NMR spectrum of the compound of Formula Ib.
Figure 12:
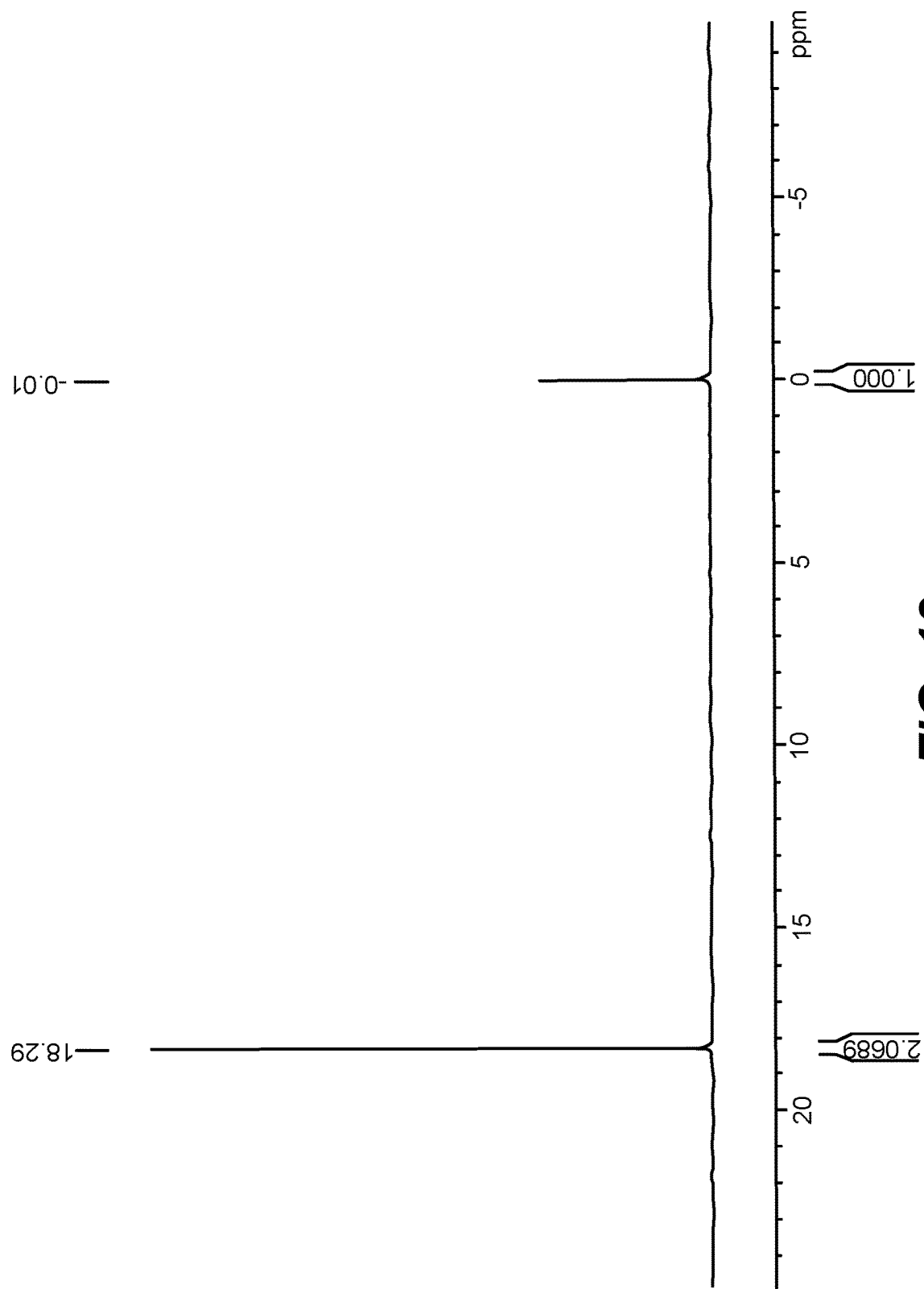
FIG. 12 shows the $^{31}$P-NMR spectrum of the compound of Formula Ib.

Prior to reaction, alendronic acid was dissolved in tetrabutylammonium hydroxide (40 wt % solution in water) and the water was removed azeotropically using toluene, followed by vacuum drying. Following alendronate-TBA preparation, DSPE-PEG2-COOH was dissolved in a mixture of 85:15 anhydrous chloroform/anhydrous dimethylformamide and warmed to 40° C. To the solution is added N-Hydroxysuccinimide (NHS), followed by 1-Ethyl-3-(3-dimethylaminopropyl)carbodiimide (EDAC), and the mixture was stirred at 40° C. for 4-6 hours. After the allotted time, $^1$H NMR spectroscopy was used to assay for DSPE-PEG2-COO—NHS ester formation (typical reaction completion was >75% by $^1$H-NMR analysis). Once DSPE PEG2 COO—NHS ester formation was confirmed, the previously prepared alendronate-TBA salt was dissolved in anhydrous chloroform and added directly to the reaction vessel, followed by triethylamine. The reaction temperature was then increased to 50° C. and allowed to stir at temperature for 18-24 hours, at which time reaction completion was assayed by TLC. Once complete, the reaction mixture was partitioned three times against 1 M aqueous hydrochloric acid to remove excess alendronate, followed by two brine washes to remove excess acid. The mixture was neutralized with ammonium hydroxide prior to bulk solvent removal via rotary evaporation. The material was then treated with Dowex® 50WX8 hydrogen form ion exchange resin to remove bulk tetrabutylammonium counterion. The resin was filtered and bulk solvent was removed from the filtrate, then the material was chromatographed with reverse phase media (methanol/water gradient) including a column wash with ammonium chloride to achieve the the compound of Formula Ib. FIG. 11 and FIG. 12 show the $^1$H-NMR and $^{31}$P-NMR spectra of the compound of Formula Ib respectively, with the structure:

Formula Ib
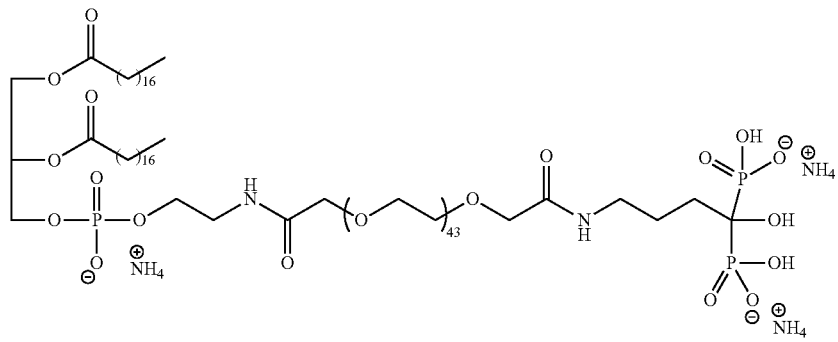
The method synthesizing of the compound of Formula Ib described herein is summarized below:
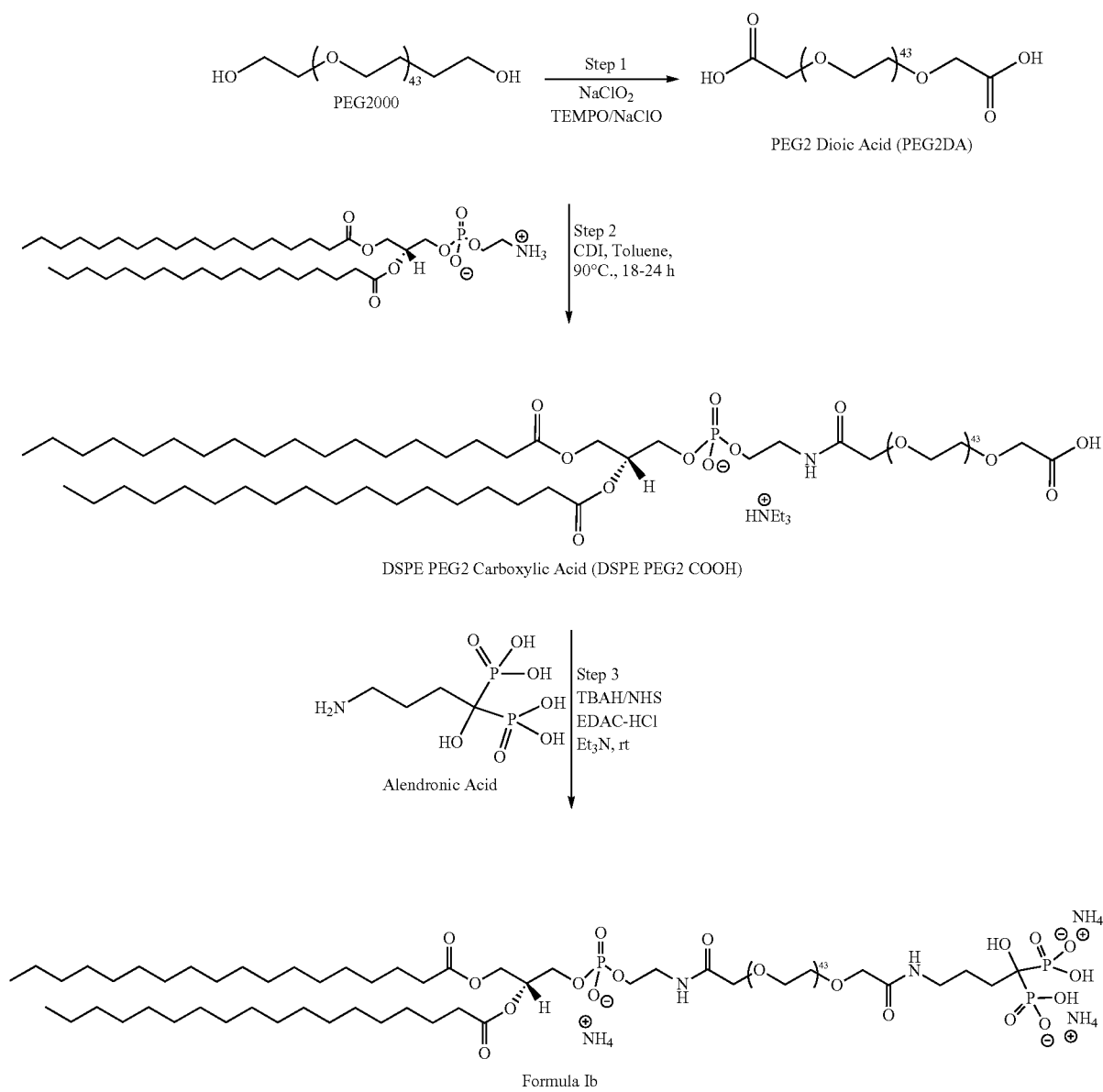

Example 2: Synthesis of Microspheres

The compound of Formula Ib generated as described in Example 1 was mixed with other lipid compositions—DSPE-PEG2k (the compound of Formula IIb)

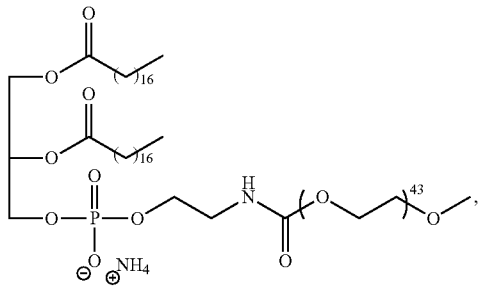

and
DSPC (the compound of Formula IIIa)

Figure 14:
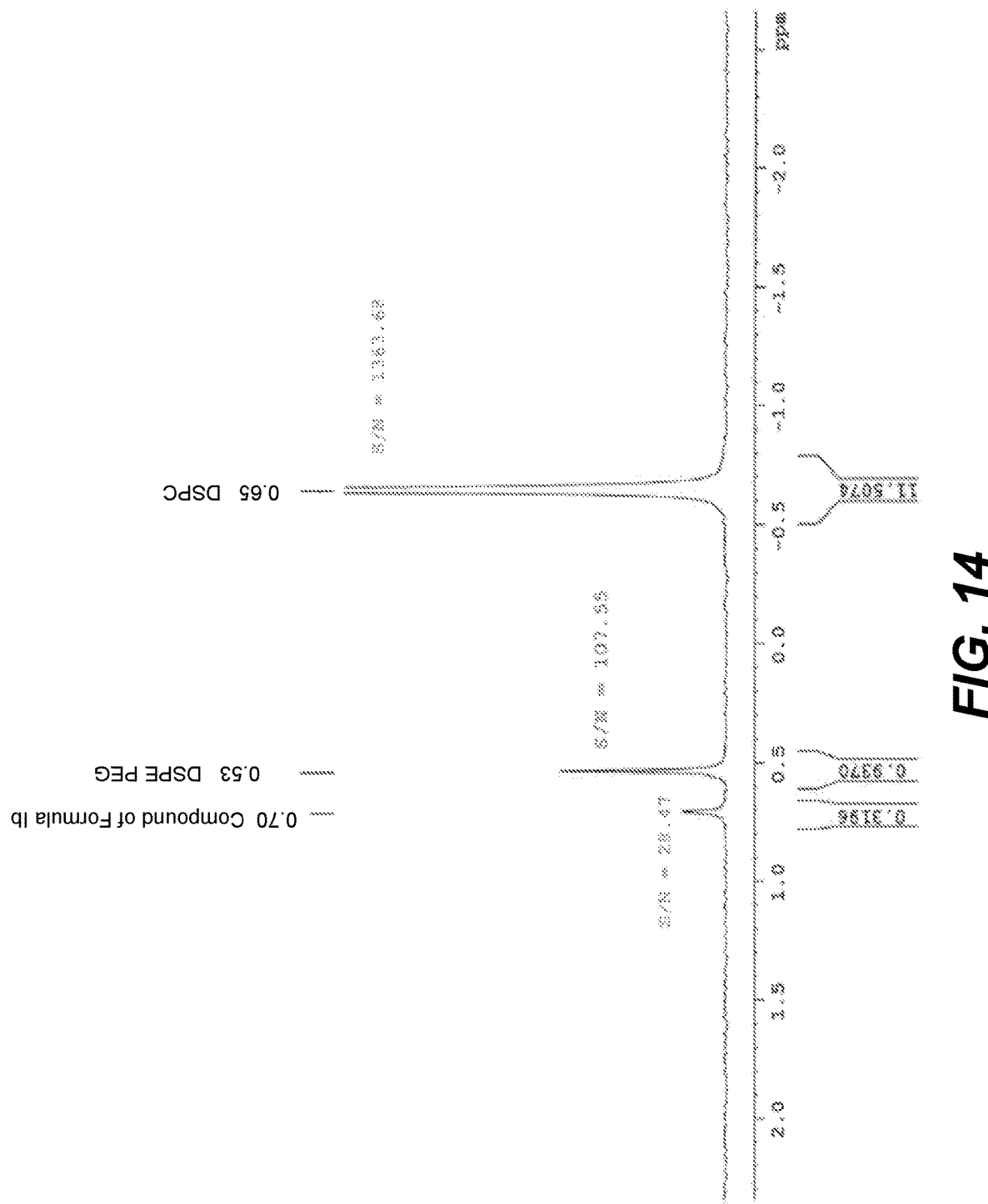
FIG. 14 shows the $^{31}$P-NMR spectrum of the liposome formulation comprising the compound of Formula Ib, 1,2-distearoyl-sn-glycero-3-phosphoethanolamine-N-[methoxy(polyethylene glycol)-2000] (ammonium salt) (DSPE-PEG2K, a compound of Formula IIb) and 1,2-distearoyl-sn-glycero-3-phosphocholine (DSPC, a compound of Formula IIIa).

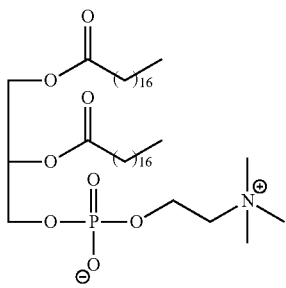

and water. $^{31}$P-NMR spectrum of the mixture (FIG. 14) shows three peaks, each corresponding to each lipid composition, the compound of Formula Ib, DSPC, or DSPE-PEG2k. Signals for each peak indicate relative amounts of the compound of Formula Ib (28.37 for "DSPE PEG Alendronate"), DSPC (1363.68 for "DSPC"), and DSPE-PEG2k (107.55 for "DSPE PEG") in the mixture.

Figure 4:
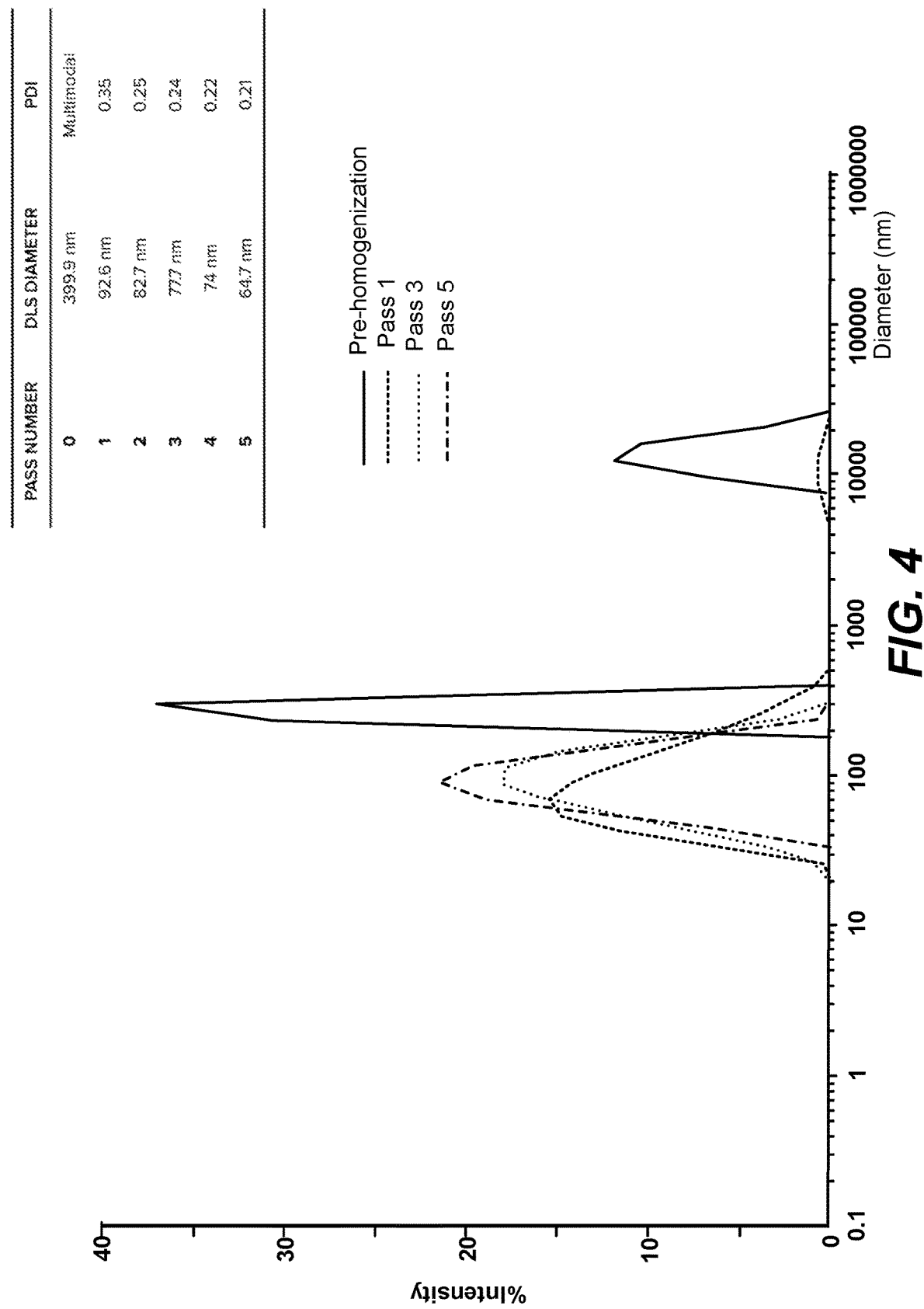
FIG. 4 shows size distributions for liquid phases of a bisphosphonate-PEG-lipid mixture measured by dynamic light scattering (DLS).
Figure 5:
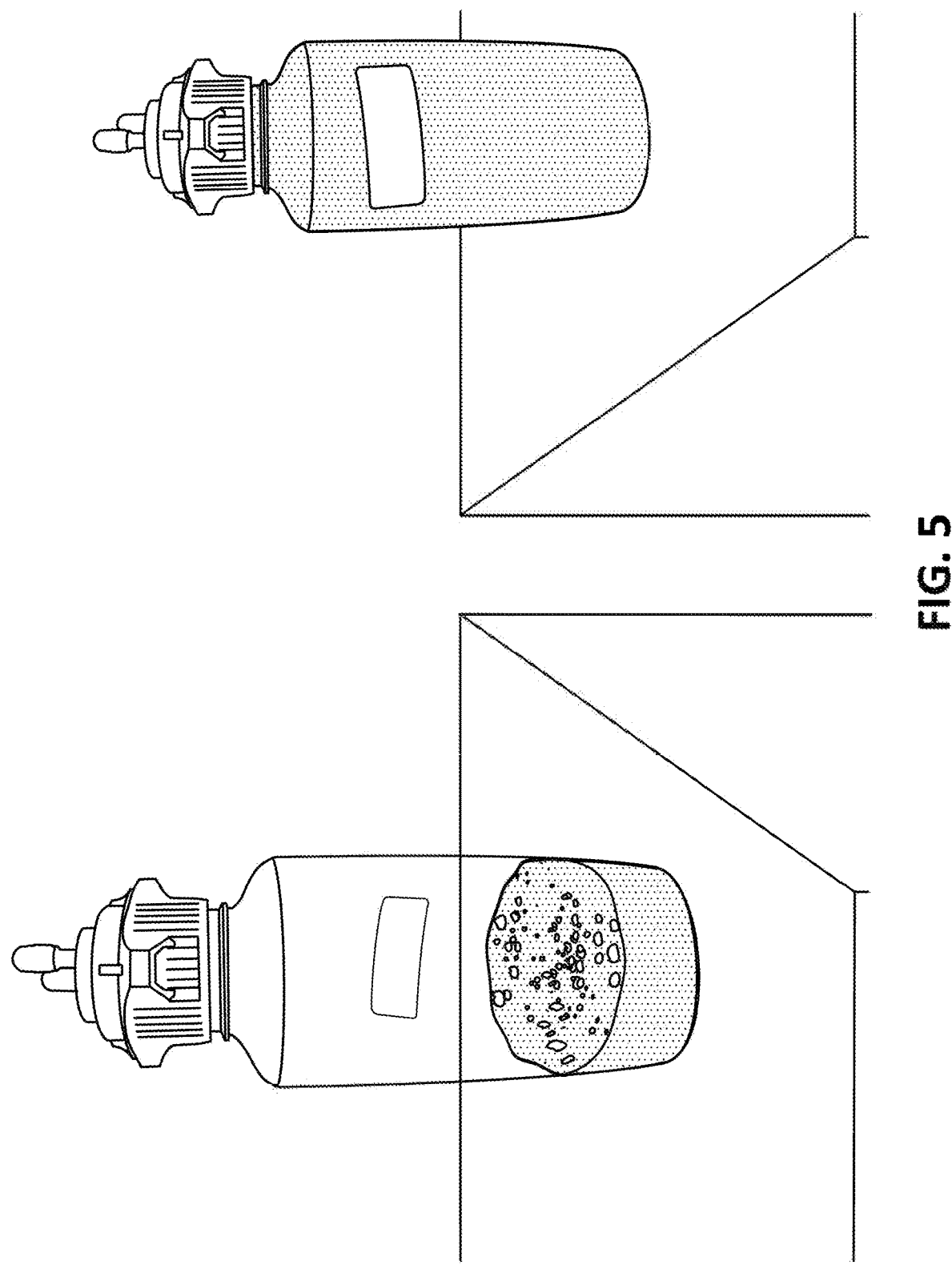
FIG. 5 shows samples of a bisphosphonate-PEG-lipid composition with gas headspace (left) and a microsphere formulation (right) of the composition described herein, illustrating qualitative differences of the two formulations.

A liquid phase of the mixture comprising the compound of Formula Ib, DSPC, and DSPE-PEG2k was processed with a homogenizer with multiple passes until the desired diameter and PDI was achieved. Samples from each pass was analyzed for size distribution using dynamic light scattering (DLS) and the result is provided in FIG. 4. The formulation is diluted in phosphate buffered saline and analyzed with a Mobius (Wyatt).

n-decafluorobutane ($C_4F_{10}$) was added to the lipid mixture and the mixture was agitated for 1-2 minutes. Images of the lipid mixture before (left) and after (right) the steps of n-decafluorobutane addition and agitation are provided and compared in FIG. 5. The images illustrate qualitative differences of the formulations.

Figure 7:
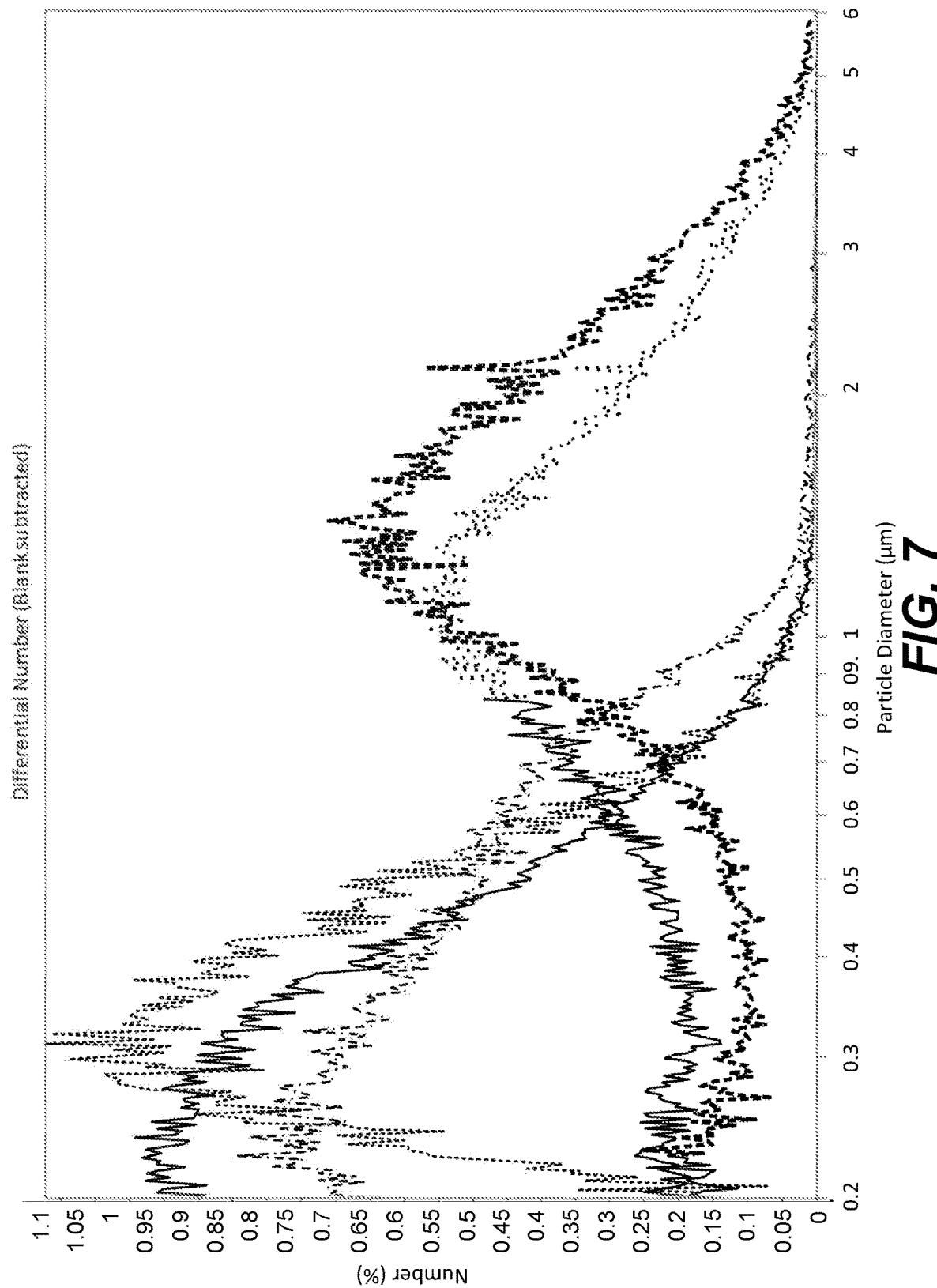
FIG. 7 shows size distribution of microspheres as measured by electrozone sensing. The number of particles (y-axis) for each bin of diameter (x-axis) is provided.

The Beckman Coulter Multisizer 4e with a 30 μm aperture was used to characterize microspheres for particle number density and particle diameter by electro-zone sensing. Sample volume ranged from 1 to 10 μL in 100 mL of IsotonII diluent. An exemplary result is provided in FIG. 7. The results show that microspheres with average sizes ranging between 0.7 and 2 μm were generated.

Example 3: Accumulation Assay

The microspheres generated as described in Examples 1 and 2 were characterized with the Beckman Coulter Multisizer 4e in a time course study while incubated with hydroxyapatite beads. Microspheres were analyzed by the Multisizer for particle density at various time points. The change in concentration of microspheres was used to calculate the number of microspheres accumulating on the surface of hydroxyapatite beads. A control microsphere sample without the compound of Formula Ib was also analyzed.

Figure 6:
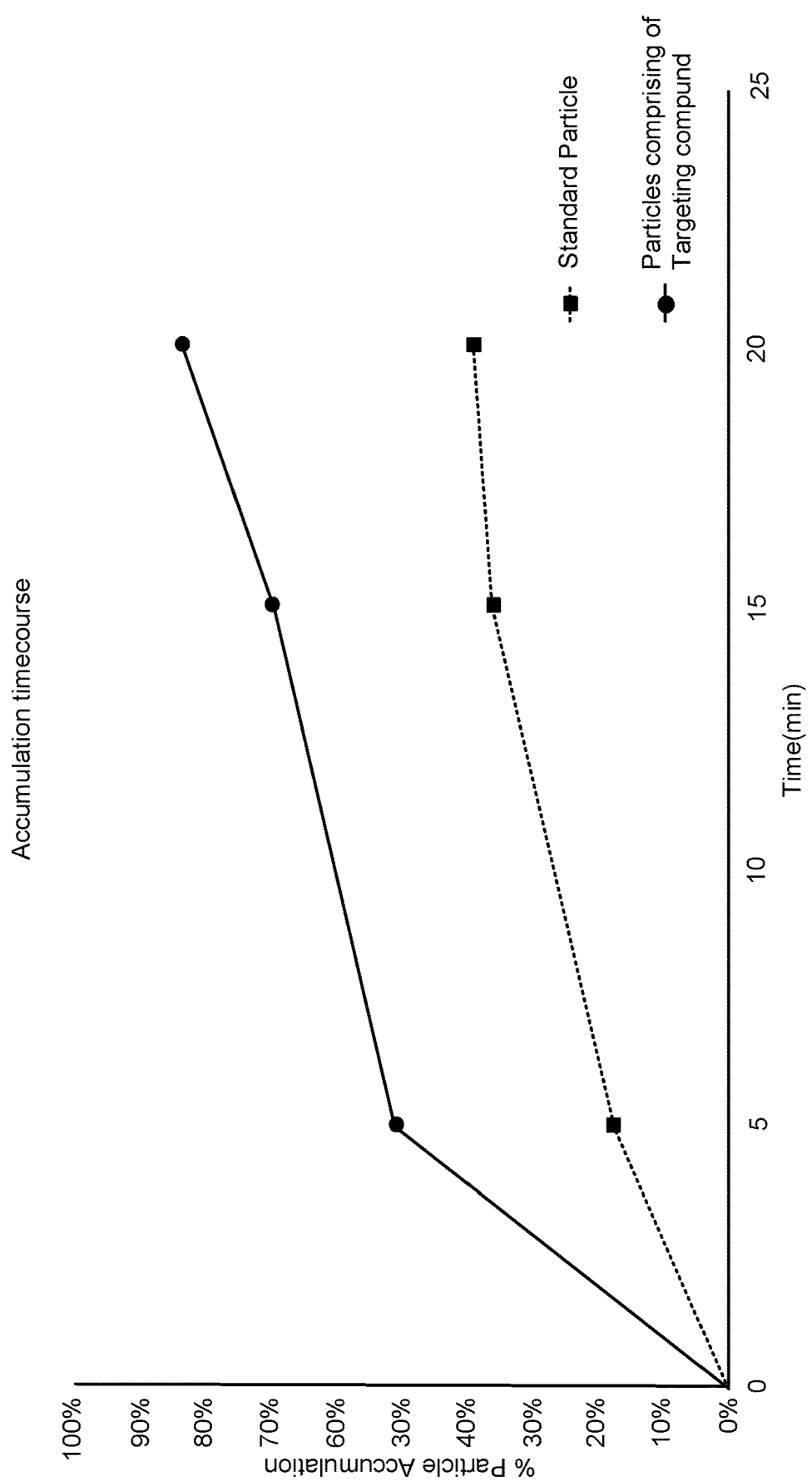
FIG. 6 is a graph showing microsphere accumulation assay results over time. The graph shows that microspheres incorporating bisphosphonate-PEG-lipid of the present disclosure have greater rates of microsphere accumulation on a mineralized surface compared to microspheres lacking bisphosphonate-PEG-lipid in the shell.

As summarized in FIG. 6, the experiment demonstrated significant accumulation of microspheres with the compound of Formula Ib onto hydroxyapatite beads over the time course study. The results suggest that microspheres comprising the compound of Formula Ib have a high affinity to hydroxyapatite beads.

Example 4: Headspace Analysis

Figure 13:
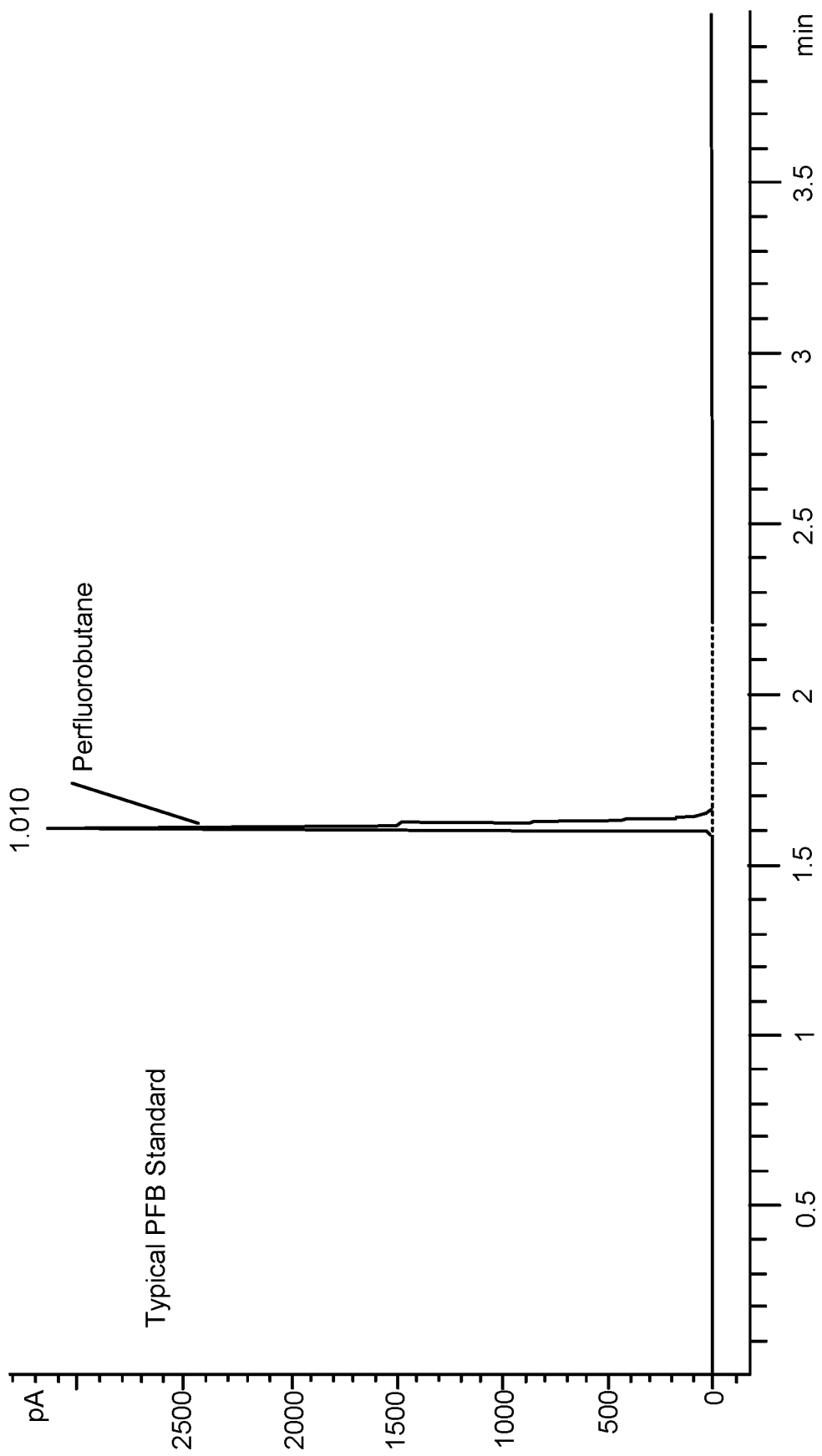
FIG. 13 shows a gas chromatograph of headspace analysis of n-decafluorobutane.

The headspace sample was pulled directly from the container containing a pharmaceutical composition of the compound of Formula Ib and n-decafluorobutane using a manual gas chromatography syringe. The headspace sample was immediately injected into the GC. GC signals from the experiment is provided in FIG. 13. It shows a peak indicating n-decafluorobutane.

Example 5: Use of Microspheres with an External Acoustic Energy Source for Treatment of Urolithiasis Microspheres generated as described in Examples 1 and 2 were administered via a cystoscopically positioned 5 Fr catheter to patients diagnosed with urinary stones. Patients had presented with acute renal colic and had a diagnosis of stone disease confirmed by CT scan. The cystoscope was removed after positioning of the catheter in the affected side of the patient's upper urinary tract and a syringe containing a microsphere solution connected to the distal end of the catheter. 0.5-1.0 mL volumes of microsphere solution were injected at multiple intervals over the course of procedures ranging in duration from 20 to 90 minutes. Acoustic energy was applied at multiple intervals over the course of the procedure. The acoustic energy source used, a SmartSphere console with a treatment head designed to be held against the skin of a patient's lower back or inguinal region, was engineered to interact with microspheres on or near stone surfaces, bringing about stone erosion, pitting and fragmentation, and had been shown to be safe in extensive studies in porcine models. Many urinary stone patients have been successfully treated using this method.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

The invention claimed is:
1. A method of treating an abnormal or obstructive mass, the method comprising:
administering to a subject with the abnormal or obstructive mass an effective amount of a microsphere com- position comprising microspheres containing fluid, so as to bring the microspheres into contact with the abnormal or obstructive mass within the subject, and directionally applying an energy to the abnormal or obstructive mass at a frequency that excites the fluid within the microspheres;

wherein the microsphere composition comprises:

a compound of Formula I

Formula I or a salt, isomer, or salt of an isomer thereof;

wherein:

n is from 10 to 30;

m is from 1 to 100; and

X is selected from the group consisting of: hydrogen, silyl, acyl, aminoacyl, thioacyl, aminocarbonyl, aminoacyl carbonyloxy, aminothiocarbonyl, aminosulfonyl, amidino, substituted sulfonyl, substituted sulfinyl, carboxy ester, phthalimido, OH, $SO_3H$ and $PO_3H$; and a pharmaceutically acceptable excipient, wherein the abnormal or obstructive mass is a urinary stone or a kidney stone.

2. The method of claim 1, wherein the microsphere composition is a reconstituted microsphere solution.

3. The method of claim 2, wherein the reconstituted microsphere solution is administered into a ureter of the subject through a urinary catheter.

4. The method of claim 1, wherein the energy is in a form of ultrasonic, electromagnetic, acoustic, microwave, laser or photonic energy.

5. The method of claim 4, wherein the energy is ultrasonic.

6. The method of claim 5, wherein the ultrasonic energy is in a frequency range from 100 kilohertz (kHz) to 2 megahertz (MHz).

7. The method of claim 5, wherein the ultrasonic energy is associated with peak pressures in a range from 0.1 MPa to 10 MPa.

8. The method of claim 1, wherein the energy is applied for a sufficient amount of time to fragment the abnormal or obstructive mass.

9. The method of claim 8, wherein the amount of time is no more than 100 minutes, no more than 90 minutes, no more than 80 minutes, more than 70 minutes, no more than 60 minutes, no more than 50 minutes, no more than 40 minutes, no more than 30 minutes, no more than 25 minutes, no more than 20 minutes, no more than 15 minutes, or no more than 10 minutes.

10. The method of claim 1, wherein the applied energy causes a change in volume of the microspheres or causes other cavitation effects of the microspheres.

11. The method of claim 10, wherein the cavitation of the microspheres causes pressure gradient changes and other mechanical effects in the abnormal or obstructive mass around the microspheres.

12. The method of claim 1, wherein the applied energy causes fragmentation of the abnormal or obstructive mass.

13. The method of claim 1, wherein the subject is human.

14. The method of claim 1, wherein the microsphere composition further comprises:

i. a compound of Formula II

Formula II or a salt, isomer, or salt of an isomer thereof; and ii. a compound of Formula III Formula III or a salt, isomer, or salt of an isomer thereof;

wherein:

t is from 10 to 30;

y is from 1 to 100; and z is from 10 to 30.

15. The method of claim 1, wherein the abnormal or obstructive mass is a urinary stone.

16. The method of claim 1, wherein the energy is in a form of laser.

* * * * *